(12) United States Patent
Hedberg et al.

(10) Patent No.: US 6,783,649 B2
(45) Date of Patent: Aug. 31, 2004

(54) HIGH THROUGHPUT CAPILLARY ELECTROPHORESIS SYSTEM

(75) Inventors: Herbert J. Hedberg, North Attleboro, MA (US); Brian Kangas, Millbury, MA (US); James L. Waters, Framingham, MA (US)

(73) Assignee: Cetek Corporation, Marlborough, MA (US)

( * ) Notice: Subject to any disclaimer, the term of this patent is extended or adjusted under 35 U.S.C. 154(b) by 148 days.

(21) Appl. No.: 10/004,973

(22) Filed: Dec. 3, 2001

(65) Prior Publication Data

US 2002/0092770 A1 Jul. 18, 2002

Related U.S. Application Data

(60) Provisional application No. 60/250,428, filed on Dec. 1, 2000.

(51) Int. Cl.[7] .................... G01N 27/26; G01N 27/447
(52) U.S. Cl. .................... 204/603; 204/451; 204/452; 204/453; 204/601; 204/602; 204/604
(58) Field of Search .................... 204/451, 452, 204/453, 601, 602, 603, 604

(56) References Cited

U.S. PATENT DOCUMENTS

| | | | |
|---|---|---|---|
| 4,927,265 A | | 5/1990 | Brownlee .................... 356/73 |
| 5,066,382 A | * | 11/1991 | Weinberger et al. ........ 204/451 |
| 5,085,757 A | | 2/1992 | Karger et al. .................... 204/299 |
| 5,198,091 A | * | 3/1993 | Burolla et al. .................... 204/601 |
| 5,198,324 A | * | 3/1993 | Yeung et al. .................... 204/452 |
| 5,364,521 A | * | 11/1994 | Zimmermann .................... 204/604 |
| 5,413,686 A | * | 5/1995 | Klein et al. .................... 204/603 |
| 5,424,037 A | | 6/1995 | Zimmermann et al. ........ 422/64 |
| 5,503,994 A | * | 4/1996 | Shear et al. .................... 436/90 |
| 5,578,460 A | | 11/1996 | Ebersole et al. .................... 435/29 |
| 5,694,215 A | * | 12/1997 | Carver .................... 356/246 |
| 5,830,659 A | * | 11/1998 | Stewart .................... 435/6 |
| 5,903,348 A | * | 5/1999 | Melman et al. .................... 356/344 |
| 5,916,428 A | * | 6/1999 | Kane et al. .................... 204/601 |
| 6,001,230 A | | 12/1999 | Burolla .................... 204/453 |
| 6,388,746 B1 | * | 5/2002 | Eriksson et al. .................... 356/318 |
| 6,475,361 B1 | * | 11/2002 | Merenkova et al. ........ 204/451 |

FOREIGN PATENT DOCUMENTS

| | | | | |
|---|---|---|---|---|
| EP | 0 448 313 | | 9/1991 | ......... G01N/27/447 |
| JP | 05 052806 | | 3/1991 | ......... G01N/27/447 |
| JP | 10 062388 | | 3/1998 | ......... G01N/27/447 |

\* cited by examiner

*Primary Examiner*—Nam Nguyen
*Assistant Examiner*—John S. Starsiak, Jr.
(74) *Attorney, Agent, or Firm*—Weingarten, Schurgin, Gagnebin & Lebovici LLP

(57) ABSTRACT

The invention is directed to a high throughput capillary electrophoresis (CE) system, which comprises multiple mobile CE detector modules that are transportable by a programmable fluid-handling arm assembly to fixed samples in microtiter plate wells for analysis. The CE system of the invention is capable of simultaneously automating sample preparation and multiple CE analysis of the sample in a continuous timely process. The CE detector modules of the invention may be equipped with any suitable detection method, such as an ultraviolet (UV) absorbance or a laser-induced fluorescence (LIF) detector.

70 Claims, 27 Drawing Sheets

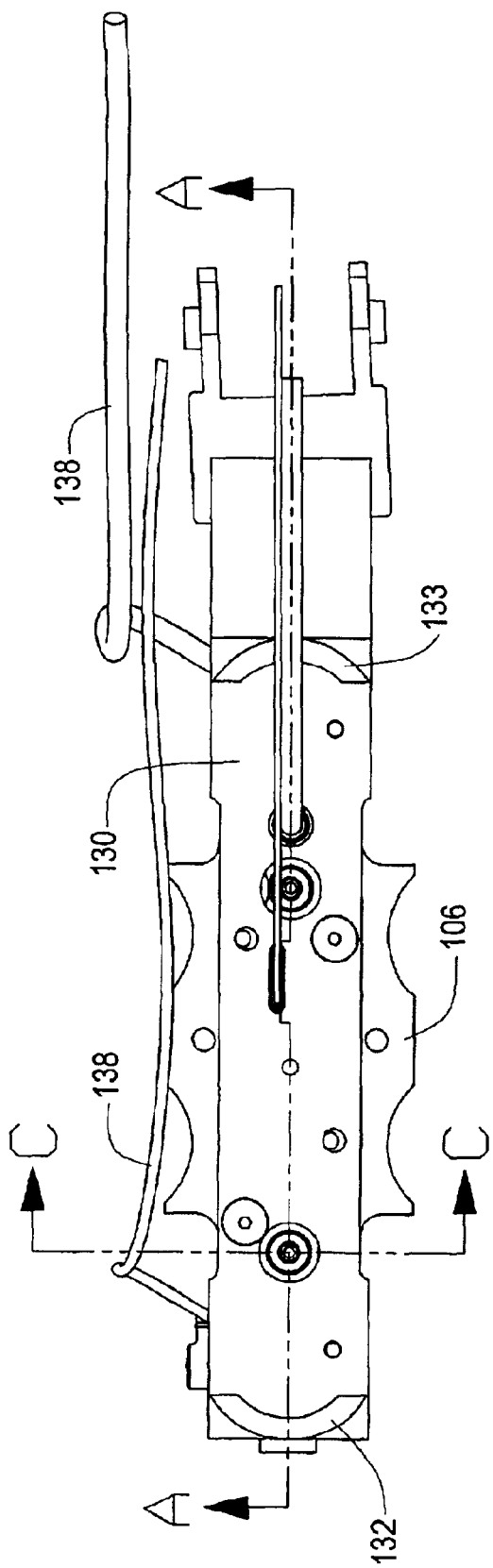
FIG. 11A
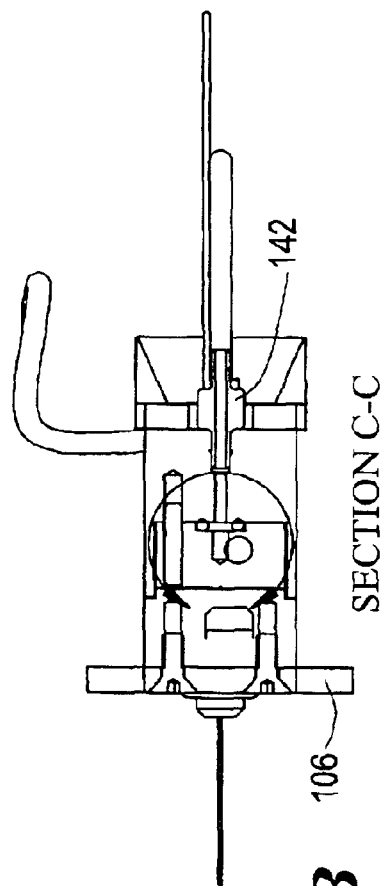
FIG. 11B SECTION C-C

SECTION A-A

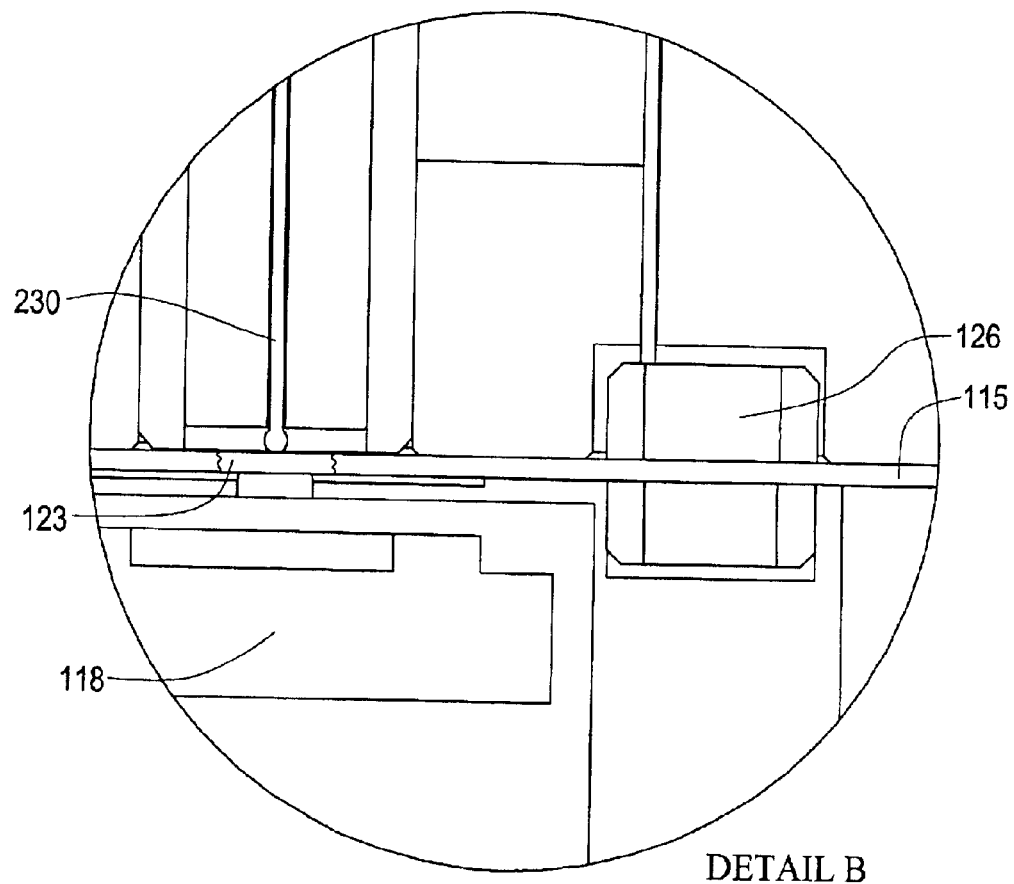
FIG. 13　DETAIL B
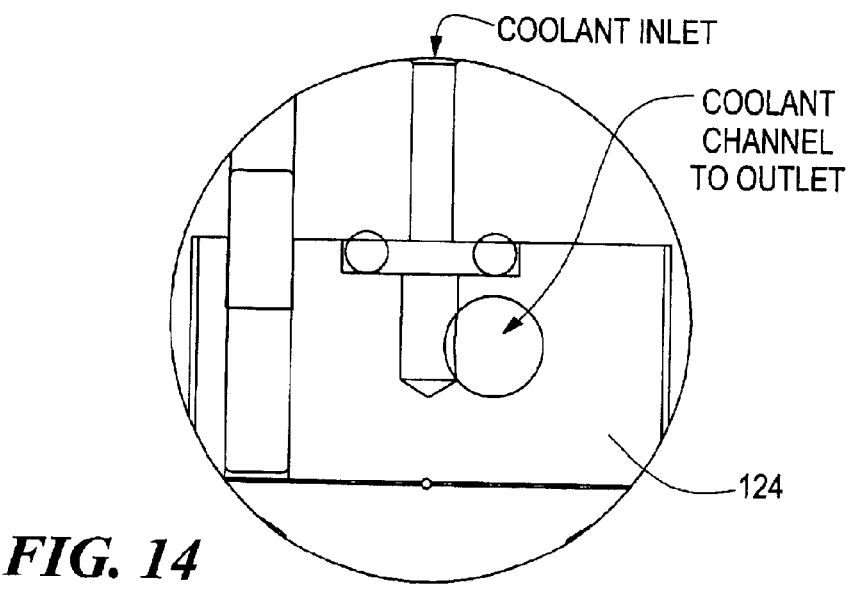
FIG. 14　DETAIL D

VIEW A-A

DETAIL B

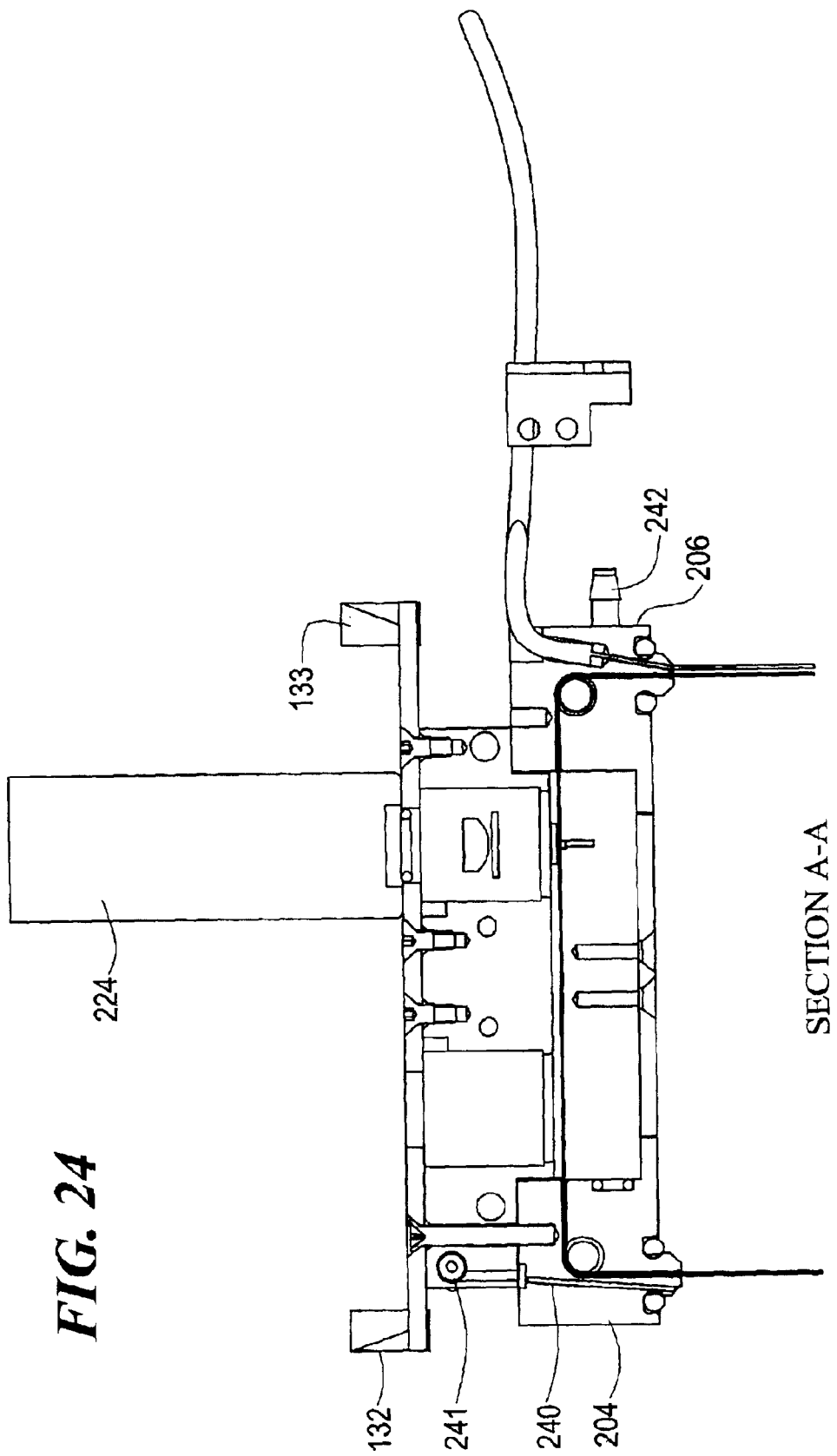

HIGH THROUGHPUT CAPILLARY ELECTROPHORESIS SYSTEM

CROSS REFERENCE TO RELATED APPLICATIONS

This application claims the benefit under 35 U.S.C. §119(e) of U.S. Provisional Patent Application No. 60/250,428 filed on Dec. 1, 2000, entitled MINIATURIZED CE DETECTOR ALLOWS TRANSPORT OF DETECTOR TO TIME-SENSITIVE SAMPLES AUTOMATICALLY PREPARED AS DETECTOR AVAILABILITY DEMANDS, the whole of which is hereby incorporated by reference herein.

BACKGROUND OF THE INVENTION

A Capillary Electrophoresis (CE) separation can be performed to determine what affinity, if any, may exist between some "interesting" target molecule and a small molecule ligand. The origin of the ligand can be from natural product samples, synthesized pure compounds in a combinatorial library, or mixtures of compounds. An exemplary method of screening complex biological materials for use in accordance with the present invention is described in Hughes et al., U.S. Pat. No. 5,783,397 (Jul. 21, 1998), the whole of which is incorporated by reference.

Performing an electrophoresis separation is not typically a process that lends itself to automation and application to high throughput screening (HTS) environments except in relatively simple applications like DNA sequencing. Historically, high sample analysis throughput rates are typically achieved by utilizing an array of capillaries which process samples in parallel. There are several disadvantages of using such multiple capillary array in a practical HTS "factory environment." The cost of producing the intricate capillary array assembly is high. The capillary array temperature can be difficult to control. Time-critical sample preparation steps must be executed for each sample at specific and repeatable times prior to the CE injection and separation event. Using a low temperature process to remove the external polyimide coating to create a sample viewing window in each of the array capillaries (which is mandatory when using capillaries with inside wall surface treatments) can be difficult. The logistics of reprocessing multiple missed samples should a single capillary in the array fail during a run can be complex. For CE systems with multiple capillaries built into a complex and expensive array assembly, if one capillary becomes defective, it is not economically feasible to immediately switch out the whole array. It will be allowed to continue running for a period of time until the number of performing capillaries drops to 90 or 80 percent of the total. In the meantime, special effort must be expended to analyze separately the samples that were to have been processed by the defective channels.

Unlike High Performance Liquid Chromatography (HPLC) separation technology where samples are inserted into the analysis stream with special valving, the volumes of sample liquid are much too small in CE to be handled in this manner. Conventionally, a CE capillary is closely integrated with an immovable ultraviolet (UV) absorbance or laser induced fluorescence (LIF) detector. Because the detector and capillary are stationary, the sample and buffer vials in most instrumentation are designed to be sufficiently mobile to provide the flexibility required for traditional CE methods. Typically, the liquid vials containing the sample, rinsing and running buffers are automatically positioned as specified by the operator's method program so as to immerse the stationary inlet and outlet ends of the capillary into the required liquids.

A typical CE affinity assay requires integrating the sample preparation process with the action of injecting the prepared sample cocktail into the CE analysis capillary. This requires, by some means, the immersion of the inlet end of the capillary into the container with the prepared sample, creating a pneumatic seal, and applying injection pressure to the contained volume above the sample liquid.

In very short, fast run-time capillary configurations where the capillary inlet can be as close as 6 cm to the detection window, it is not feasible to mechanically isolate the capillary injection point (the capillary inlet end) from the detection window with its associated detector optics. For this reason, existing CE instruments use complex mechanical arrangements to transport each sample vial to the inlet end of the capillary because the capillary must be fixed to the relatively massive detector mechanism.

SUMMARY OF THE INVENTION

The present invention relates to a high throughput screening (HTS) capillary electrophoresis (CE) system comprising a plurality of miniaturized mobile detector modules. The detector modules of the invention are transported by a programmable robotic arm assembly to an area of fixed sample wells for analysis. The arm assembly is also capable of integrating sample preparation simultaneously and independently of the CE analysis. The invention achieves high throughput CE assay, which requires a complex series of precise sample preparation steps, resulting in a time critical injection window, followed immediately with CE injection, separation, and data collection processes.

The miniaturized detector modules contain a single capillary precluding any maintenance of an intricate multi-capillary assembly. The operation of a single detector may be paused as soon as any degradation in the electrophoretic performance is observed without affecting the throughput and productivity of the remaining active detectors. This is not only cost-effective but it also reduces the extra expense of sample preparation materials, and the time and effort of repeating the defective sample analysis.

The capillary in the miniaturized detector module is also temperature controlled. Maintaining a controlled capillary temperature results in consistent and accurate separation analysis. Depending on the CE assay, some commercially available capillaries are distinctly temperature sensitive, deleteriously affecting the performance of the capillary. As one embodiment, the detector modules of the invention contain a heat sink to absorb extraneous heat as well as a channel for liquid coolant to circulate, maintaining a constant temperature environment for the capillary. A low temperature process is also used to remove the external polyimide coating on, for example, fused silica capillary for creating a separation detection window.

The detector modules of the CE system of the invention are adapted to include any type of detection, preferably an ultraviolet (UV) absorbance detection or a laser-induced fluorescence (LIF) detection. Other types of detection include, but not limited to, visible light absorbance, fluorescence polarization, conductivity, radioactive, and electrochemical detection. The detector modules are configured to increase sensitivity of detection by customizing the optics assembly for the detectors as well as modifying the internal detection area for decreasing extraneous light energy.

The CE system of the invention is fully programmable and automated by a controller assembly, which is interfaced with the arm assembly and the miniaturized detector modules. The CE system is programmed to handle time-critical sample preparation steps required prior to CE sample injection and separation analysis. Sample preparation and analysis are coordinated to produce HTS CE results by having a single microfluidic pipette on the arm assembly work in concert with a plurality of miniaturized detector modules. After a sample is prepared with the single pipette resource, one detector module can analyze the sample, while the same pipette prepares another sample for analysis by a different detector module. Maximum throughput is established by balancing the sample preparation time with the analysis time for the whole system. For example, if a given assay requires four minutes of analysis time and one minute of sample preparation time, then four detectors would be configured with a single pipette.

Accordingly, such an efficient and versatile CE system of the invention increases throughput of CE assays as well as the sensitivity and repeatability of the assays as more fully described below.

BRIEF DESCRIPTION OF THE DRAWINGS

Other features and advantages of the invention will be apparent from the following description of the preferred embodiments thereof and from the claims, taken in conjunction with the accompanying drawings, in which:

FIG. 11A is a top view of the upper housing of the UV detector module of FIG. 6;

FIG. 11B is a cross-sectional view of the UV detector module along line C—C of FIG. 11A;

FIG. 13 is a partial view of Detail B of FIG. 12, which shows the positioning of the UV light source compared to the capillary and the capillary retainer plug;

FIG. 14 is a partial view of the Detail D of FIG. 11B, which depicts a cross section of the coolant channel in the heat sink;

FIG. 24 is a cross-sectional view along line A—A of FIG. 22;

DETAILED DESCRIPTION OF THE INVENTION

Figure 1A:
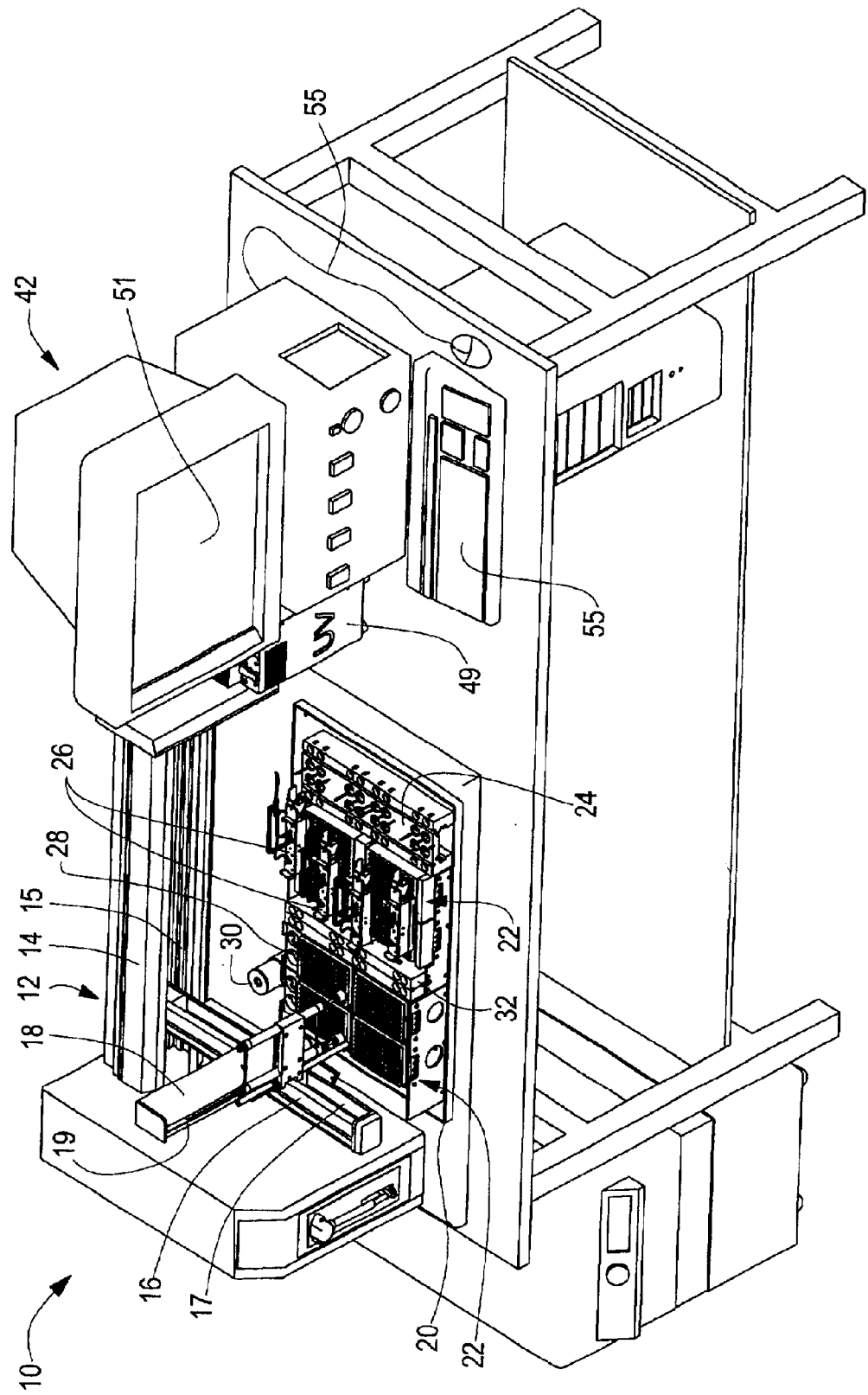
FIG. 1A is an isometric view of a capillary electrophoresis (CE) system of the invention showing an exemplary ultraviolet (UV) version.
Figure 1B:
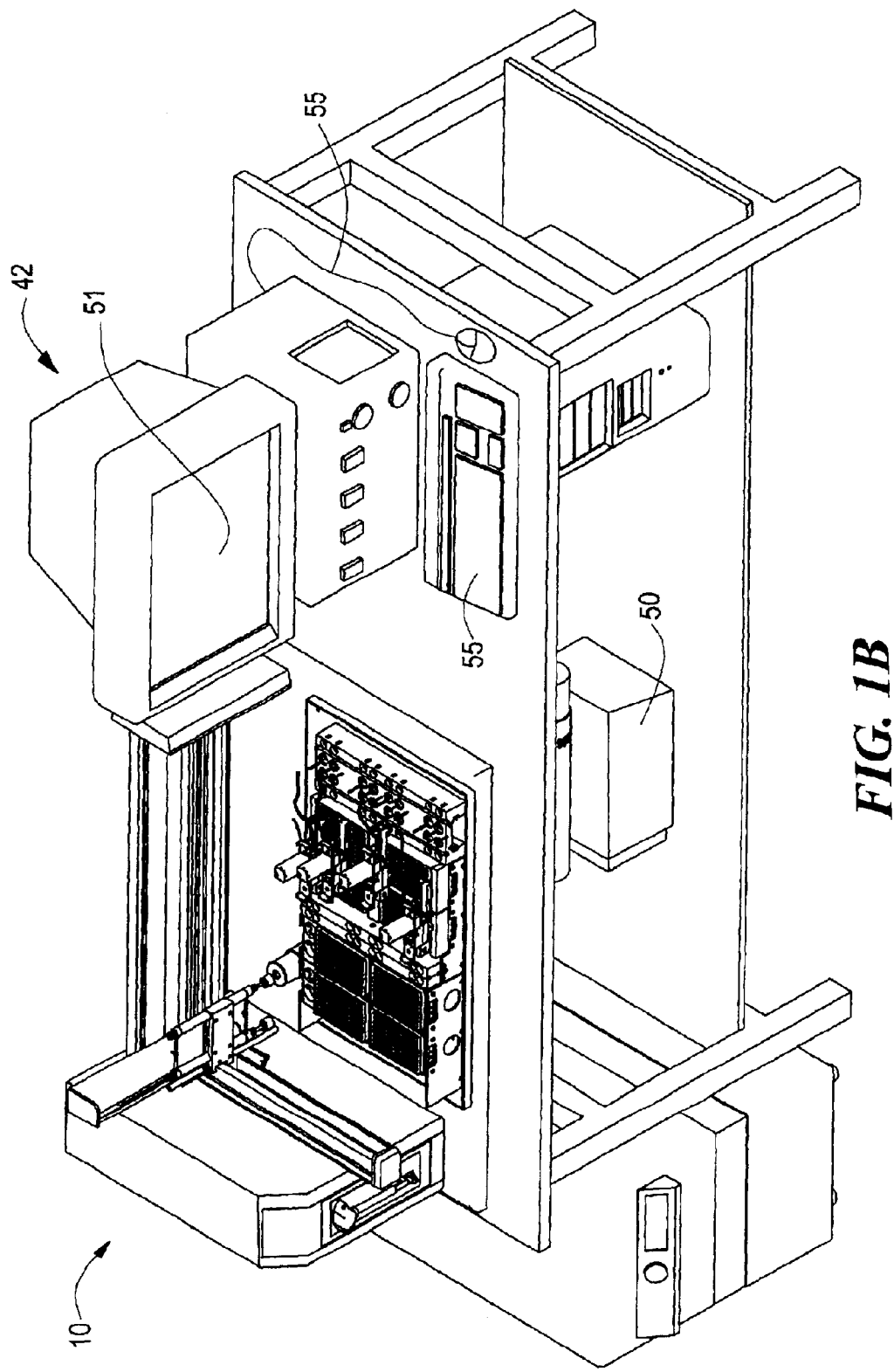
FIG. 1B is an isometric view of a CE system of the invention showing an exemplary laser-induced fluorescence (LIF) version.

A high throughput Capillary Electrophoresis (CE) system according to the invention includes multiple mobile CE detector modules that are transportable by a programmable, movable, fluid-handling arm assembly. The system of the invention establishes high throughput screening by automating sample preparation and multiple sample CE analysis in a continuous timely process. This process is achieved by providing closely coupled integration between a single microfluidic pipette resource and multiple CE detector modules. After the pipette prepares the sample to be analyzed in a stationary sample container, a CE detector module of the invention moves to the sample vial to perform the analysis, rather than transporting individual vials to a stationary capillary/detector arrangement as in prior art CE systems. High CE assay throughput is also achieved by having a single pipette and multiple detectors operating both simultaneously and independently on a common instrument platform such that the pipette resource capacity is balanced with the detector resource capacity. For example, a single pipette might process 50 samples per hour, while four detectors might also process 50 samples per hour. Maximum system throughput is achieved when neither resource creates a bottleneck.

A high throughput CE system according to the invention is shown generally in FIGS. 1A–5. The system 10 includes a base 20 upon which an array of microtiter plates 22 is arranged. Into each the microtiter plates 22, a plurality of vials or wells are molded, for example, from polypropylene or polystyrene, in which target molecules and sample molecules or molecular ligands are contained for use during an analysis, as known in the art. Alternatively, specialized microtiter plates may include one or more insertable vials. A detector docking station 24 is provided on the base 20 along one side of the microtiter plate array. A plurality of the moveable detector modules 26 is dockable at the docking station. Each detector module 26 includes a suitable detector, such as an ultraviolet absorbance detector or a laser induced fluorescence detector. Other types of detectors may be provided on the detector modules, for example, visible light absorbance, fluorescence polarization, conductivity, radioactive, and electrochemical detection.

Figure 4:
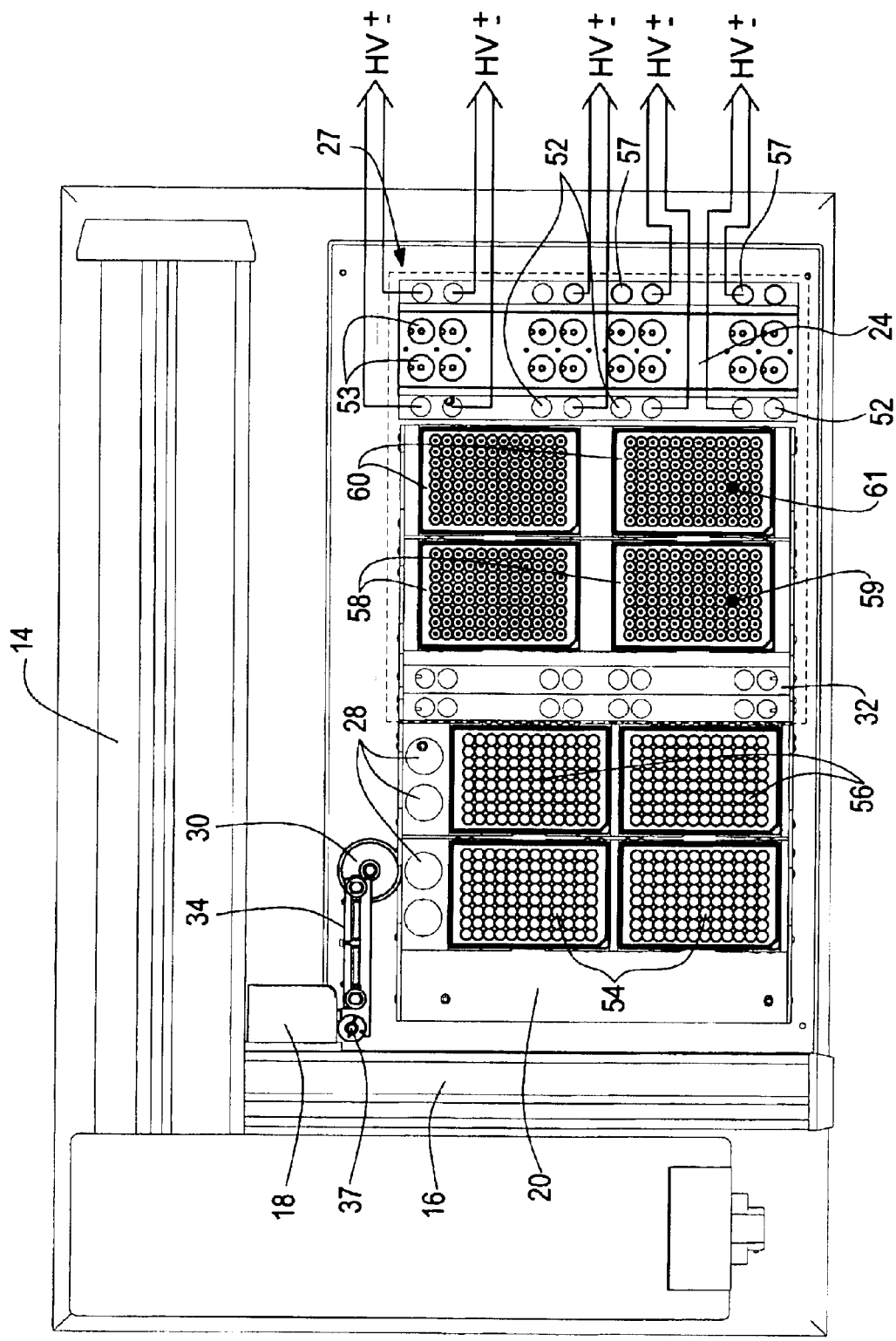
FIG. 4 is a partial top view of the CE system of FIGS. 1A and 1B showing an exemplary miniaturized detector movement boundary 27.
Figure 5:
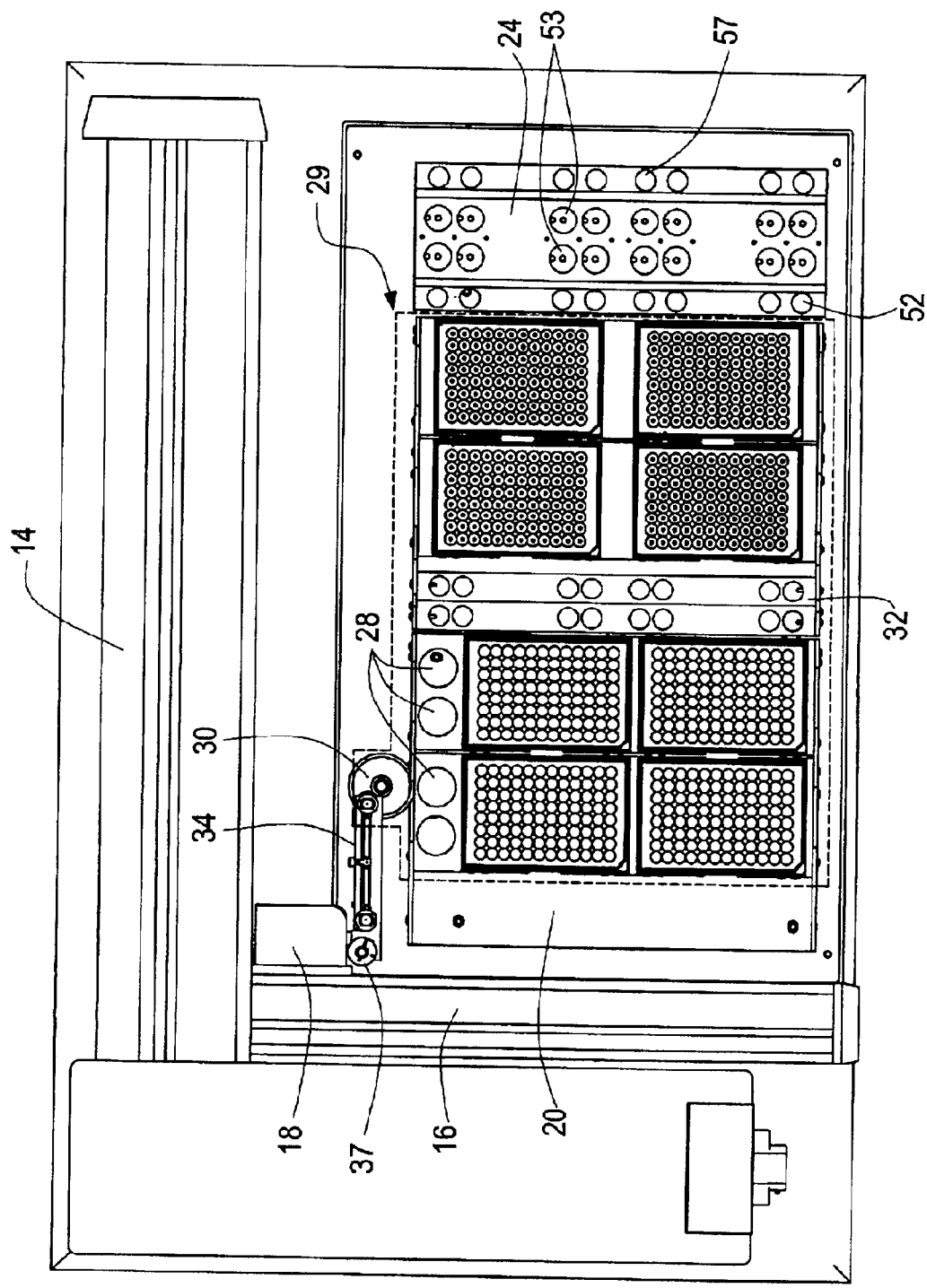
FIG. 5 is a partial top view of the CE system of FIGS. 1A and 1B showing an exemplary pipette movement boundary 29.

The arm assembly 12 is mounted on the base 20 to provide movement in three orthogonal directions, the X-direction, the Y-direction, and the Z-direction. The arm assembly 12 is operative to pick up a detector module 26 from the docking station 24 and move it to a desired location on the base, such as to a position over the microtiter plates, as discussed further below. The base 20 also includes a buffer supply station 28, a pipette wash station 30, and an injection mixture station 32 holding a plurality of vials arranged along another side of the microtiter plate array. The arm assembly may access these stations at various times during an analysis, depending on the particular analysis to be performed, as known in the art. The arm assembly 12 also includes a pipette 37 for movement to appropriate stations or vials in the microtiter plate array for appropriate aspiration and dispense of liquids for sample preparation, also as known in the art. A commercially-available disposable pipette tip 35 attached to the pipette 37 may be used for any liquid aspiration and dispense. The pipette tip 35 may also be notched at an angle to ensure full immersion to the bottom of the sample vials or wells. FIGS. 4 and 5 show a suitable outer boundary 27 for motion of the detector modules 26 and a suitable outer boundary 29 for motion of the pipette 37. These boundaries may be adjusted to accommodate any desired arrangement of the microtiter plate array and the various other stations.

More particularly, the arm assembly 12 includes a X-arm 14 supported on the base 20 to the side of the microtiter plates and stations. The X-arm 14 is elongated to extend in the X-direction and includes a track mechanism 15 along its length. An Y-arm 16 is movably mounted for travel along the track mechanism 15 on the X-arm 14. The Y-arm 16 is cantilevered from the X-arm 14 to extend in the Y-direction over the stations and the array of microtiter plates. The Y-arm 16 also includes a track mechanism 17 extending along its length in the Y-direction. A vertical or Z-arm 18 is movably mounted for travel along the Y-direction track mechanism 17. The Z-arm 18 similarly includes a track mechanism 19 extending vertically along its length in the Z-direction. A pick-up assembly 34 is mounted for vertical travel along the vertical track mechanism 19 of the Z-arm 18. The pipette 37 is also mounted for vertical travel on the Z-arm 18. In the embodiment shown, the motions of the X-arm 14, Y-arm 16, and the Z-arm 18 are controlled electrically. The pick-up assembly 34 is controlled pneumatically. The motion of any axis or mechanism may be controlled in other ways, such as hydraulically or magnetically. Similarly, the arm assembly 12 may be configured in other ways, such as a single robotic arm movable in three dimensions, as will be appreciated by those of skill in the art. The arm assembly 12 may also include a bar code reader 36 for appropriate identification and location of any sample at any stage of the analytical process. A bar code reader 36 may be mounted, for example, on the Z-arm 18.

The pick-up assembly 34 includes a mechanism 41 for retaining or lifting a detector module 26. In the embodiment shown in Fig. 2C, the retaining mechanism includes a pair of pneumatically operable piston 38 and cylinder rods 39 having magnetic solenoids 40 fixed at their ends. The magnetic solenoids 40 contact and attach to a magnetizable element disposed on each of the detector modules 26 for the purpose of magnetic lifting. The magnetizable element may be a magnetizable plate, which may be metal such as a steel. Any other suitable retaining mechanism may be provided.

A detector module 26 suitable for use in the present invention is described here generally in conjunction with a ultraviolet (UV) detector module, although it will be appreciated that any desired type of detector may be provided in the detector module. An UV detector module and a laser-induced fluorescence (LIF) detector module will be described more specifically below.

In general, each detector module 26 has a capillary 108/109 (see FIGS. 6–8) extending from an inlet end 114 to an outlet end 116 of the detector module 26. The capillary includes an inlet end 108 that protrudes from the inlet end 114 of the detector module and an outlet end 109 that protrudes from the outlet end 116 of the detector module. The detector modules comprise an upper housing 104 and a removable cartridge component 102 that can be removed when the capillary needs replacing and so that a fresh cartridge component with a fresh capillary can be maintained in reserve and quickly replaced in a detector module. The capillary is laid in an appropriately sized channel 121 formed in an upper surface of the cartridge component and a corresponding channel formed in the lower surface of an upper housing of the detector. A first electrode 110 is provided at the inlet end 114 of each detector module, and a second electrode 111 is provided at the outlet end 116 of each detector module. The capillary inlet 108 and associated electrode 110 are located substantially together such that both may be inserted in a single well on the microtiter plate array 22. Similarly, the capillary outlet end 109 and associated electrode 111 are located substantially together such that both may be inserted in a single well on the microtiter plate array 22.

Figure 7A:
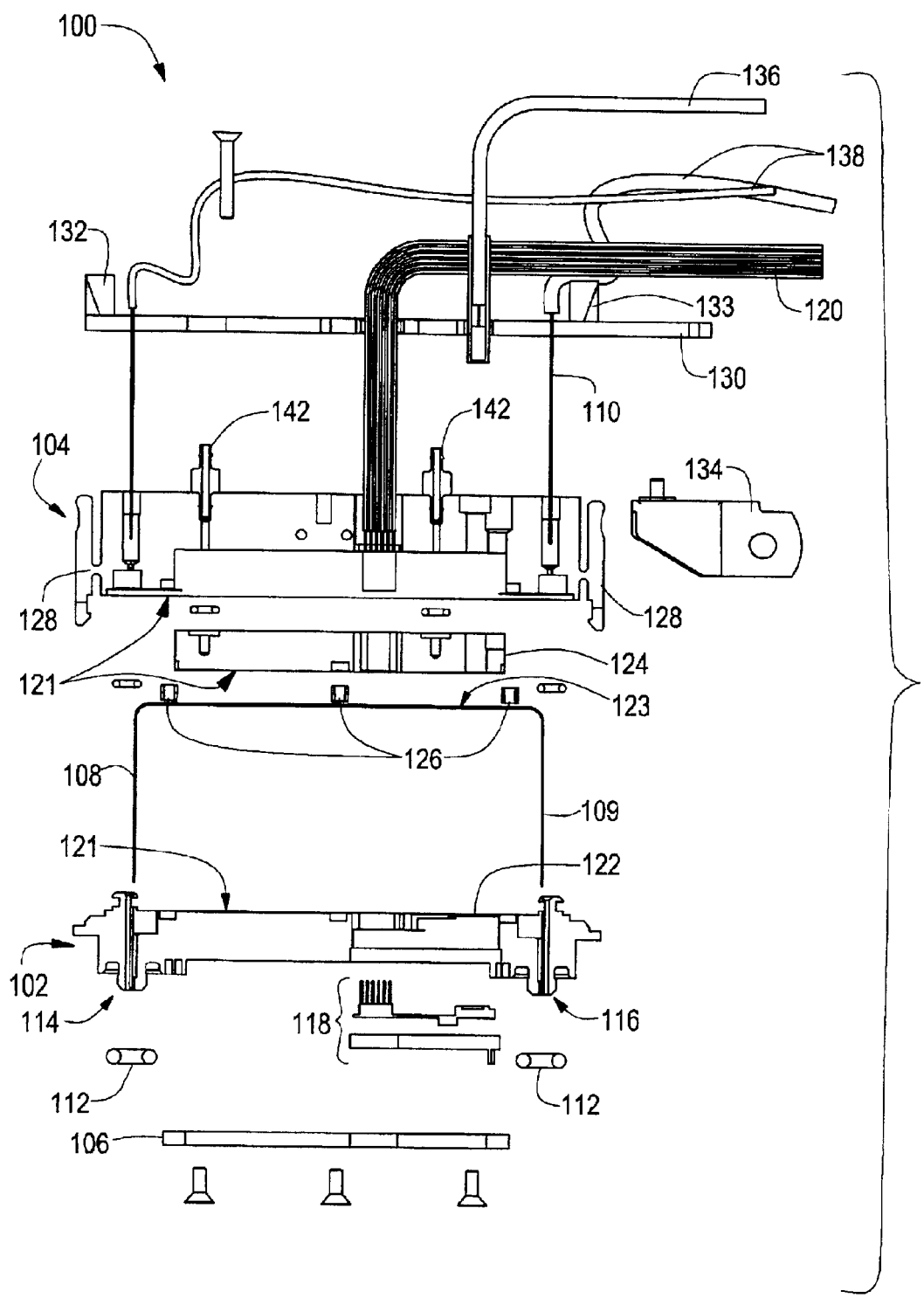
FIG. 7A is an exploded schematic view of the UV detector module of FIG. 6.
Figure 8:
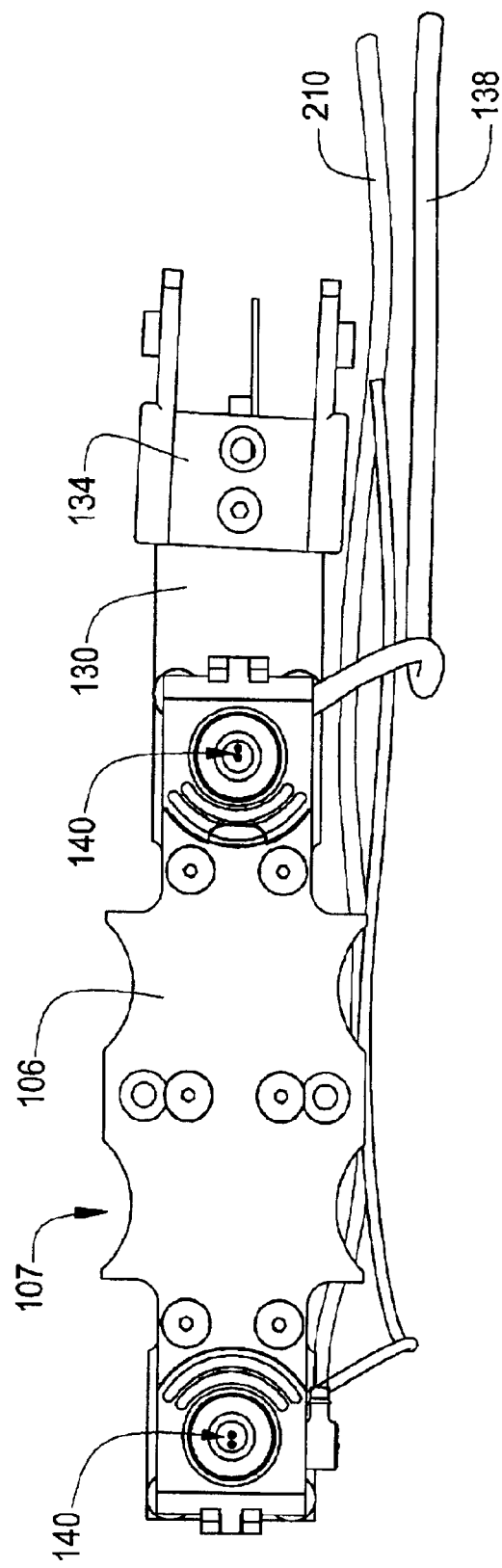
FIG. 8 is a bottom view of the UV detector module of FIG. 6.
Figure 10:
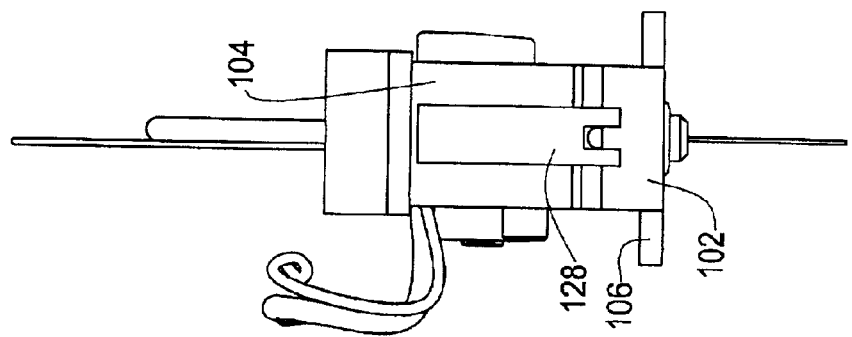
FIG. 10 is side view of the UV detector module of FIG. 6.
Figure 9:
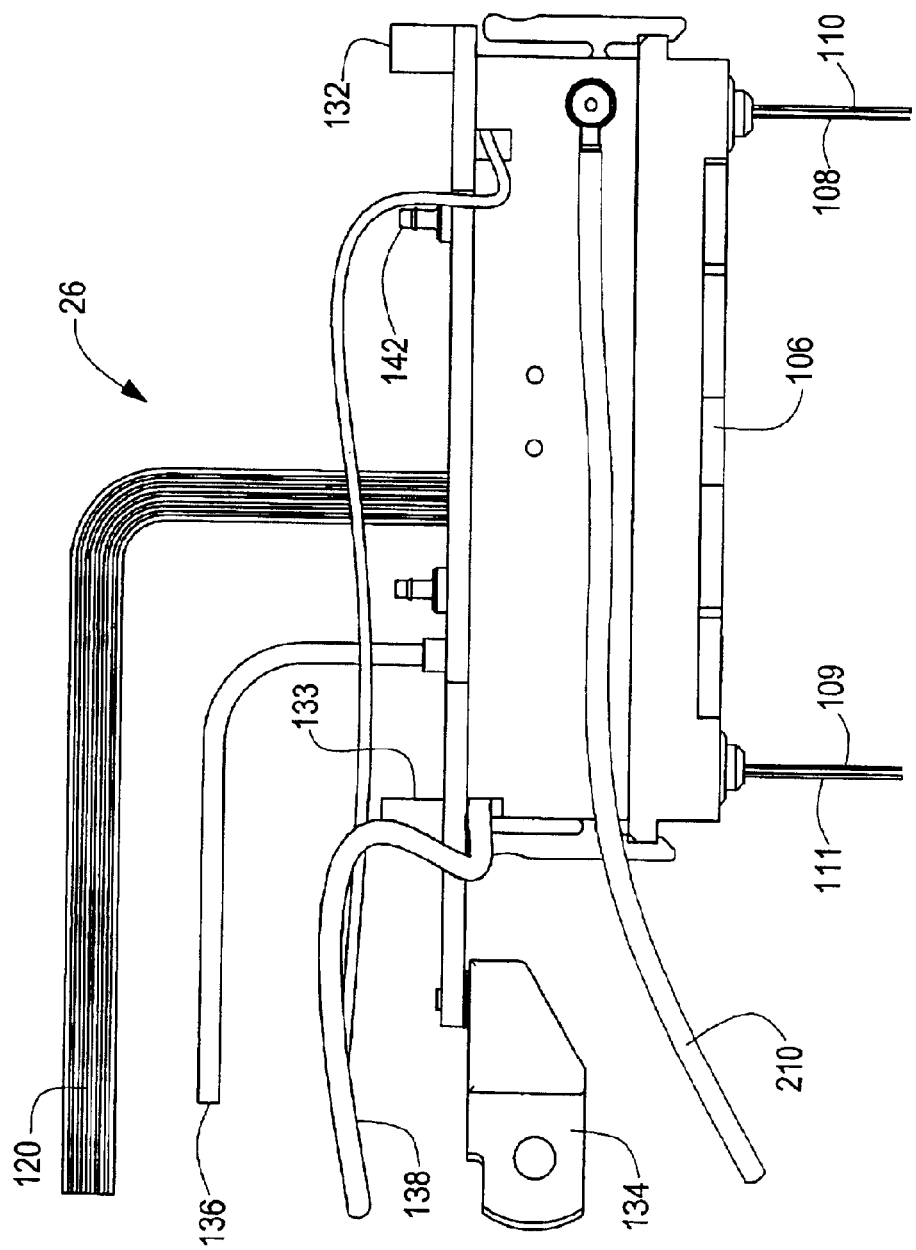
FIG. 9 is a back view of the UV detector module of FIG. 6.

Each detector module includes a desired detector assembly such as a UV detector 100 (as shown in FIG. 7A), discussed further below. A window 123 is formed in the capillary 108 such that the window 123 is aligned with the desired detector for sample separation detection. The window, approximately 8 mm in length, is formed in an external polyimide coating on a fused silica capillary using a suitable tool by mechanically removing a strip of the external polyimide coating from the outside of the fused silica tube. Exemplary capillaries are made from narrow diameter fused silica tubing of various inside and outside diameter configurations. The polyimide coating is added to make the normally brittle fused silica somewhat flexible to provide for normal handling and installation procedures. Other types of capillaries are commercially available. Depending on the type of assay required, other means of providing a window on the capillary may be used such as laser ablation and hot sulfuric acid processes, as known in the art.

The detector modules 26 of the invention are sufficiently miniaturized so that they can operate simultaneously and independently on a common instrument platform. The detector modules 26 are sufficiently small and lightweight so that the arm assembly 12 can readily transport the detector modules 26 to a fixed liquid-containing vial among an array of fixed-position vials and/or microtiter plates. The mobility of the miniaturized detector modules 26 also allows for access to the liquid vials to perform a variety of sample preparation steps prior to the actual CE injection for analysis. Accordingly, the same arm assembly 12 is involved in the sample preparation in conjunction with the pipette 37.

Each detector module 26 contains a single temperature-controlled capillary to address two key constraints relative to the goal of achieving maximum throughput from a CE system. The CE affinity technology requires that the inside surface of the capillary be treated to mask certain functional groups from the chemistry. This precludes utilizing any heat process to remove the polyimide coating from an assembled capillary array in order to form the detection window. Further, if multiple capillaries are arranged side-by-side in some array cartridge, it is not possible to completely remove the polyimide coating by mechanical means in order to form the windows. If the capillary window is formed before mounting an individual capillary in an array cartridge, significant breakage will occur because of the fragile window section. Additionally, natural samples can cause a high failure rate of the capillary. Accordingly, it was not desirable to commit multiple capillaries to a single non-repairable assembly. Conversely, in this invention, changing a defective capillary in one detector can occur without affecting the continued operation of the sample preparation pipette and the other three detectors. This capability provides the highest possible level of productivity from the CE system of the invention. Similarly, because individual capillaries are replaced before sample data are unresolvable, minimal repeat injections are required.

Figure 1C:
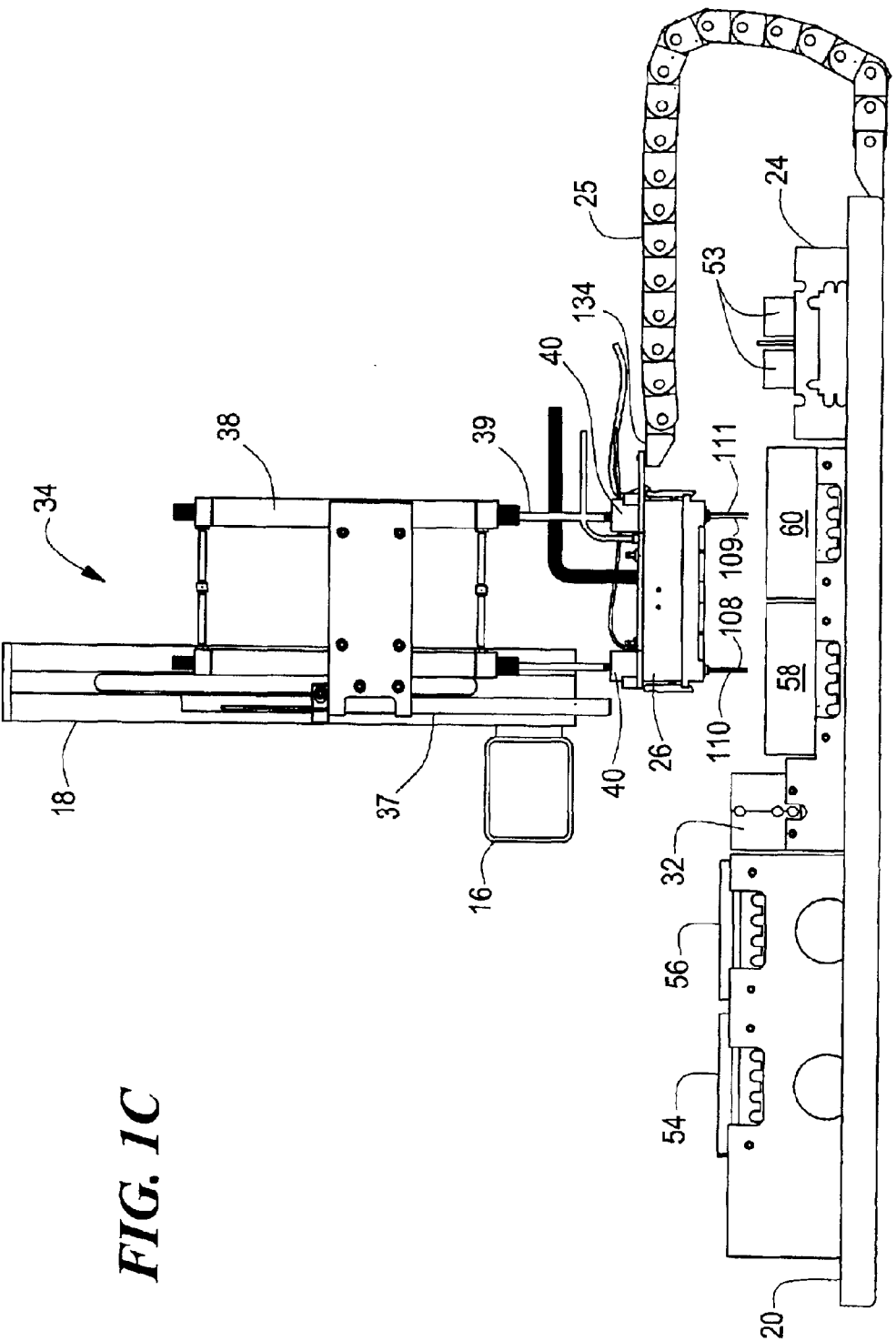
FIG. 1C is a front view of a miniaturized mobile detector module in an exemplary UV version attached to the base of the CE system of FIGS. 1A and 1B.
Figure 2A:
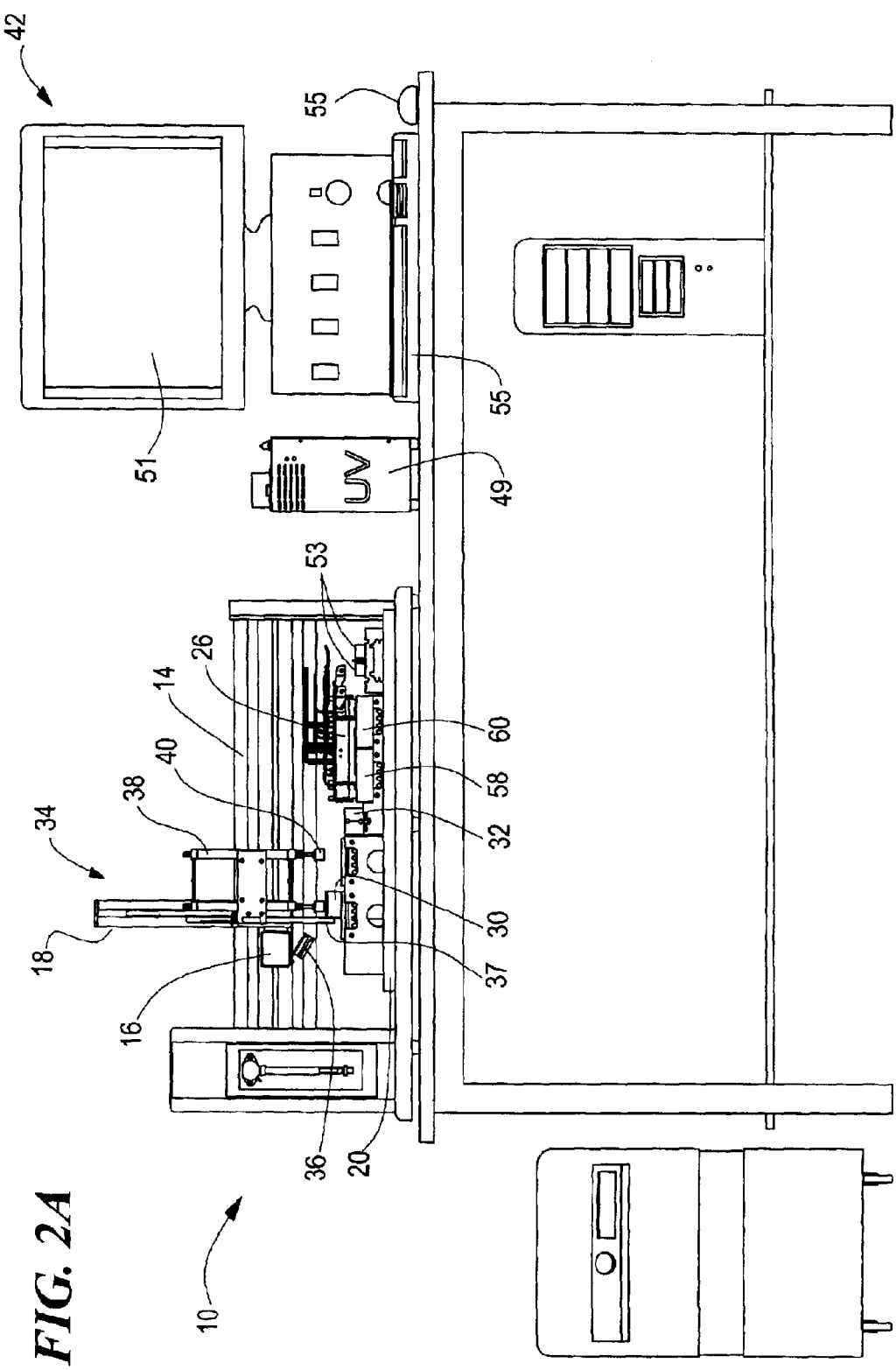
FIG. 2A is a front view of the CE system of FIG. 1A.
Figure 2B:
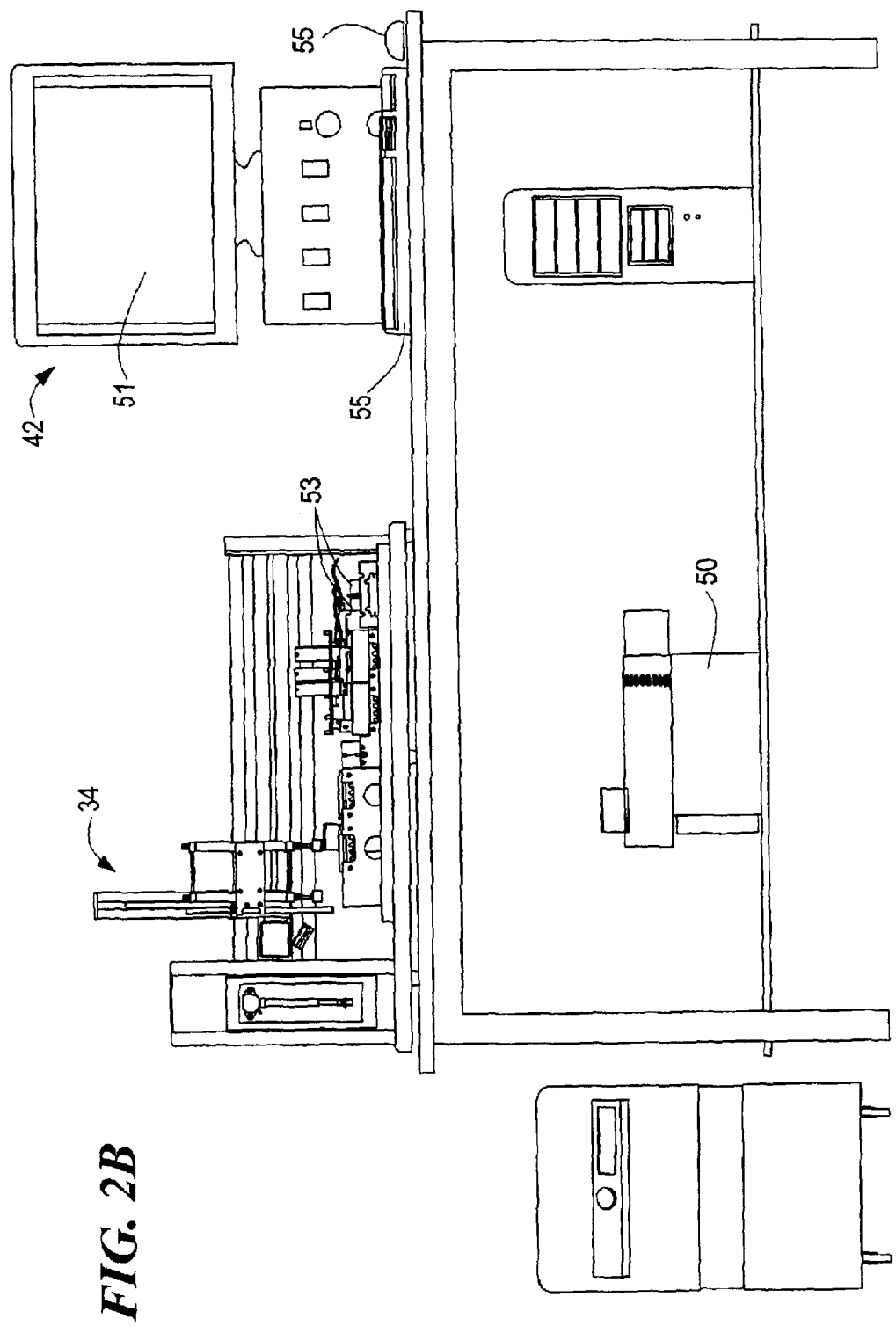
FIG. 2B is a front view of the CE system of FIG. 1B.
Figure 2C:
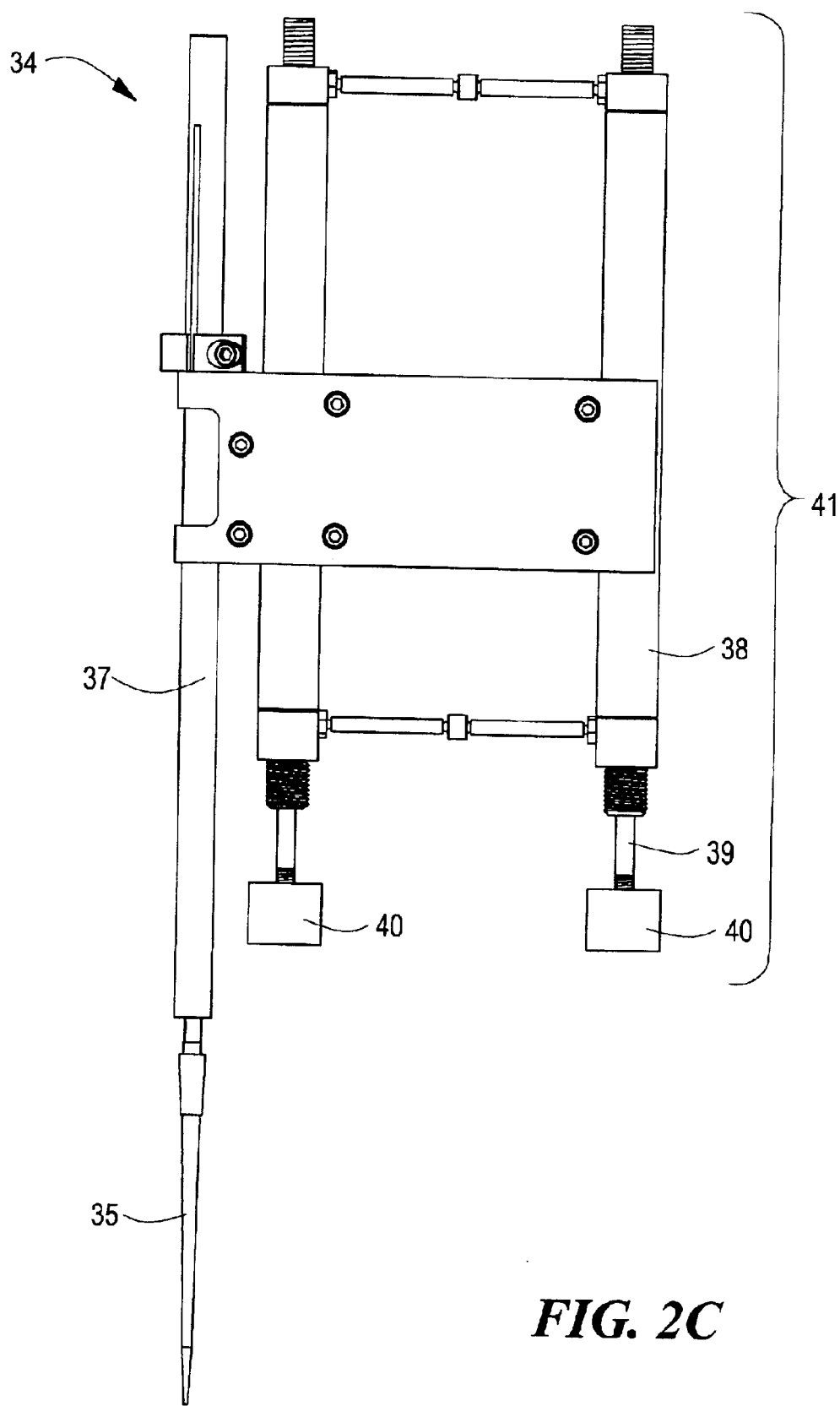
FIG. 2C is a front view of the pick-up assembly of the CE system of FIGS. 1A and 1B.
Figure 3:
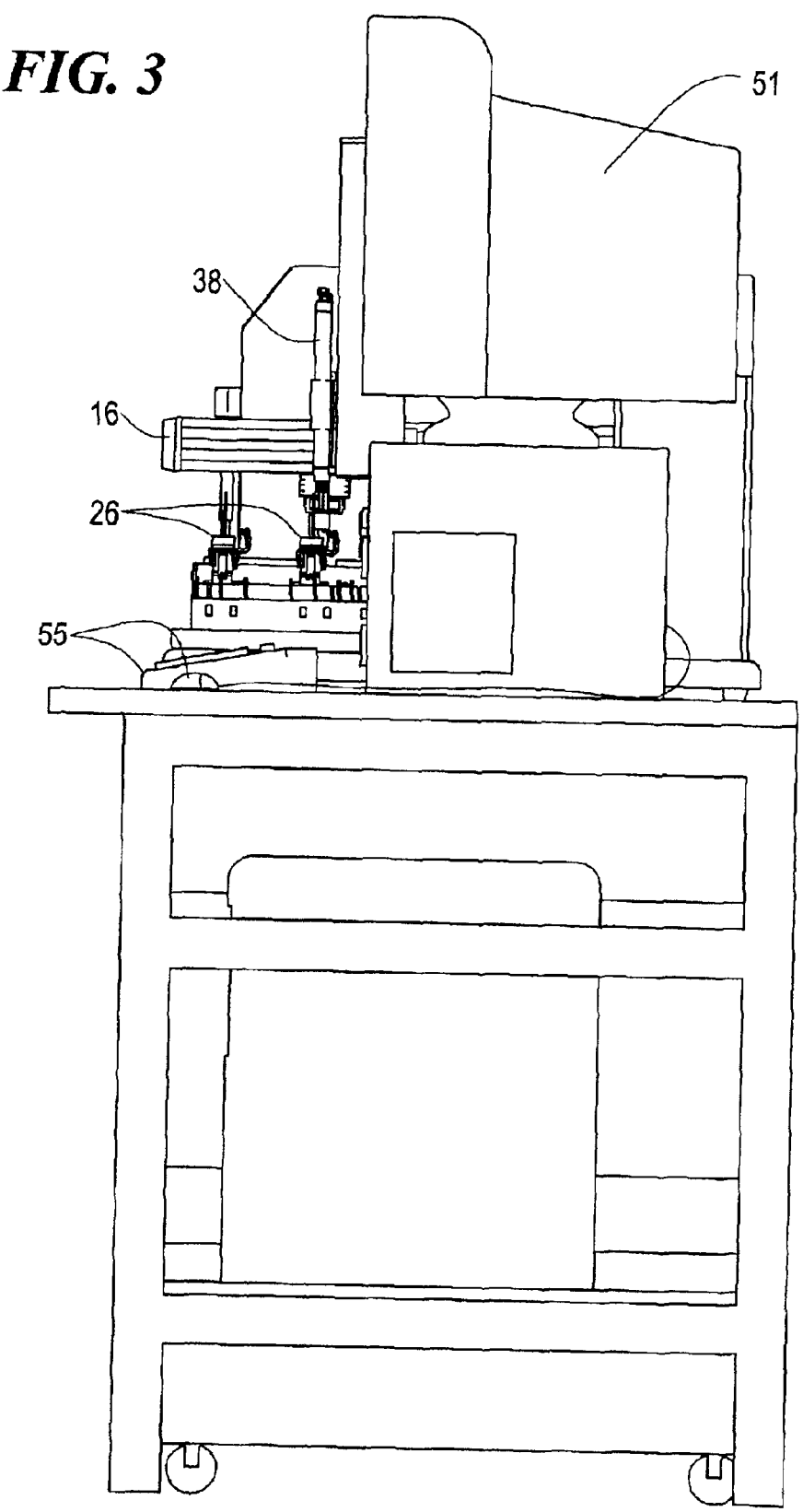
FIG. 3 is a side view of the CE system of FIG. 1A.

The detector modules 26, when not in use, are docked at the detector docking station 24. The arm assembly 12 lifts and repositions a detector by energizing the magnetic solenoids 40 and bringing them into contact with a magnetizable pick-up plate 130 of the detector modules 26. The detector docking station 24 includes corresponding inlet buffer vials 52 for receiving the capillary/electrode inlet (108 and 110) and outlet buffer vials 57 for the capillary/electrode outlet (109 and 111) ends of the detector modules. The docking station 24 also includes a detector hold-down mechanism, such as a pair of energizable magnets 53 disposed to contact corresponding docking magnetizable hold-down plate 106 on the detector modules 26. The detector hold-down mechanism is de-energized when the magnetically operable retaining mechanism on the pick-up assembly 34 is energized to pick up a detector module. Cabling for operation of the detector modules, such as fiber optic cables, high voltage power cables, signal cables, tubing for coolants and/or water, and pneumatic tubing, extends from one end of each detector module to appropriate ports on the base. A cable guide 25 (as shown in FIG. 1C) is preferably provided to retain the cabling from the detector module to the ports to prevent tangling and ease movement of the detector modules 26.

The CE system of the invention includes a controller assembly 42 that is operative to control, typically via appropriately programmed software, the movements of the arm assembly 12, aspirate and dispense operations of the pipette, and transport and operation of the detector modules 26. A graphical user interface (GUI) is preferably provided to allow a user, such as an application chemist, to conveniently author a method program which instructs the CE system to execute a desired sequence of liquid handling and CE analysis steps. Subsequently, an unskilled instrument operator can cause the CE system to execute the saved method program resulting in the desired analytical result. The controller assembly 42 includes typical components of a computer system, such as a display device 51 such as a monitor, input devices 55 such as a keyboard and a mouse, and a processor and memory. Other components, such as a UV lamp 49 or LIF laser detector light source 50, are also located conveniently near the system. In this manner, the user, such as a laboratory technician with little or no chemistry nor programming background, may direct the system to perform sample method steps and view the analysis results on the display device in real time. Additionally, if any degradation in the electrophoretic performance is observed, the user can pause the operation of a single detector module, for example, to replace the capillary, discussed further below, without affecting the throughput and productivity of the pipette mechanism nor the remaining detectors.

The arrangement of the CE system of the present invention allows the allocation of pipette and detector resources to the tasks of processing samples to be fully managed by the control assembly using any suitable optimization algorithm, as known in the art. In this manner, a single fluid-handling resource 37 is coordinated with the multiple detector modules 26 so as to load balance the fluid handling tasks of the assay and the separation/analysis part of the assay. Maximum productivity (assay throughput) is achieved when maximum resources are applied to the rate limiting (bottlenecking) part of the process. By adding detector resources until the rate of the analysis exceeds that of the sample preparation, assay productivity can be maximized.

In the embodiment shown in FIGS. 4 and 5, the first two microtiter plates 54 contain control samples. The control sample provides a periodic reference electropherogram that is used during the evaluation and ranking session for comparison with the electropherograms of unknown samples.

The next two microtiter plates 56 stores samples containing the potential unknown drug candidate or ligand. Sources of samples may generally come from natural products, synthetic compounds, and compounds formulated through combinatorial chemistry techniques. Natural products may also include, but not limited to, extracts of terrestrial plants, extracts of marine plants, cells from higher animals including humans, eubacteria, actinomycetes, bacteria, extracts from non-recombinant or recombinant microorganisms, microbial fermentation broths, fungi, protozoa, algae, archaebacteria, worms, insects, marine organisms, sponges, corals, crustaceans, viruses, phages, tissues, organs, blood, soil, sea water, water from a fresh-water body, humus, detritus, manure, mud, and sewage or partially purified fractions thereof. Desirable traits include moderate solubility in water and low molecular weight. The results of the CE assay screen will indicate if there exists any affinity of the sample molecule for the target molecule. Typically 1% of screened samples will register some level of interaction with a given target molecule.

Center vials 32 on the base 20 contain, inter alia, target molecules of interest, to be analyzed with natural extract samples contained in the sample plates 56. Exemplary target molecules include, but not limited to, DNA or RNA (used to search for nucleic acid-binding proteins, transcription factors, etc.) ribosomes, cell membrane proteins, growth factors, cell messengers, telomerases, elastin, virulence factors, antibodies, replicases, other protein kinases, transcription factors, repair enzymes, stress proteins, uncharacterized disease-related genes and/or their RNA and protein products, uncharacterized disease-related regulatory DNA or RNA sequences, lectins, hormones, metabolic enzymes, proteases and toxins. The molecule may be chemically, enzymatically, or recombinantly altered to improve its electrophoretic properties (e.g., deglycosylated), or subjected to fluorophore or polyion addition to facilitate its separation and/or detection during CE. The center vials 32 on the base 20 may also include running buffer, rinsing buffer, and other reagents depending on the analysis.

The next two microtiter plates 58 are inlet working plates provided to supply a mixture of an aliquot of a target sample from the center vials 32 and an aliquot of a natural extract sample from the sample plates 56 prepared by the pipette mechanism, and transferred by the pipette mechanism to a working well 59. The capillary inlet 108 and its associated electrode 110 of a detector immerse into the well 59 for sample injection and analysis.

In certain assays, the sample volume is small, for example, 5 µl. To ensure that capillary electrode/capillary are immersed in the sample, the well includes a V-bottomed container supported on by a compression spring for compliance to adjust the height of the V-bottom container to the exact length to the capillary/electrode pair. By pressing on the top plate of the detector module by the Z-arm, a pneumatic seal is created against the top surface of the inlet working plate, as discussed above and applying an injection pressure to the sealed container, the liquid in the V-bottom vial is forced into the capillary because the spring compliance assures that the capillary is immersed in the liquid.

The next two microtiter plates 60 are outlet working plates intended to provide wells for receiving the discharge from the capillary outlet 109 of a detector. The inlet plates 58 and the outlet working plates 60 are arranged such that spacing between two corresponding reservoirs of the inlet and outlet microtiter plates is the same as the spacing between the inlet and outlet ends of the capillary installed in the detector module 26. For example, as shown in FIG. 4, the spacing between well 59 in the inlet working plate 58 and between well 61 in the outlet working plate 60 is approximately the same as the distance between the inlet 108 and the outlet 109 ends of the capillary that is installed in the detector module. In this manner, the detector can be inserted into two corresponding wells simultaneously to allow the material in the inlet plate well 59 to flow through the capillary either by pneumatic pressure or by electrophoretic means, generate an analytical result, and discharge the material into the outlet plate well 61.

In operation, with all the control plates 54 and the sample plates 56 in place, empty inlet and outlet working plates 58 and 60 installed, running buffer reservoir 28 filled, target injection vials 32 refreshed, the detector modules 26 are initially docked at the docking station 24. The capillary/electrode inlet ends 114 and outlet ends 116 of the detector modules 26 are immersed in the corresponding inlet buffer vials 52 and outlet buffer vials 57. Sample preparation is begun by the arm assembly 12 initially moving the pipette 37 to the pipette wash station 30 for appropriate rinsing. Then the arm assembly 12 begins diluting with running buffer, taken from the running buffer reservoir 28, the contents of a control plate 54 or a sample plate 56 well. The diluted mixture is aspirated, transferred, and dispensed 50% into an inlet working plate well and 50% into the corresponding outlet working plate well. After dispensing the sample mixture from the pipette, the arm assembly then moves the pipette to the wash station 30 for cleaning prior to starting to dilute the next control or sample.

In certain cases, sample preparation may involve more than just a simple dilution operation. For example, if a competitive ligand is being used to develop a competitive assay, then some incubation time delay is probably required after the addition of the sample to the existing target/ligand mixture complex. After a sample mixture is prepared, in certain cases, a relatively short incubation time of a few seconds to a few minutes is required to allow competitive reactions among the sample components to reach equilibrium. After equilibrium has been achieved, but before excessive incubation time results in inconsistent assay results, the CE injection is made and the analytical separation is performed. Accurate reproducibility of the incubation time, defined as the point of addition of the sample or ligand to the point the complex is removed from the equilibrium solution by the injection event is critical to recognizing affinity effects through comparison with negative control injections. The CE system of the invention can repeat this interval with a variation of less than 0.5 seconds among one-minute incubations.

The arm assembly 12 is then activated to transfer a selected detector module 26 from the detector docking station 24 to the appropriate wells in the working plates 58, 60. The lifting mechanism is energized to pick up the detector module 26, while de-energizing the hold-down mechanism at the docking station 24. These mechanisms are electromagnetic in this case, but could be various electromechanical devices. The arm assembly 12 moves the capillary/electrode inlet end of the detector module 26 to a selected sample/mixture well and the capillary/electrode outlet end of the detector module 26 to the corresponding discharge well in the working microtiter plates 58 and 60. The Z-axis lowers the detector module into the well pair and applies sufficient pressure to the top of the detector such that a pneumatic seal is created with an inlet o-ring 112 (FIG. 7) caught between the underside of the detector module and the top surface of the inlet working plate. A sealing mechanism is provided to seal the detector modules 26 to the working wells. For example, the rubber O-rings 112 centrally located around the capillary/electrode inlet and outlet ends provide a seal for applicable pressure to rinse sample solution diluted with buffer (typically several uL) through the capillary (typically 10.0 psi for 30 seconds with a 50 µm inner diameter capillary).

When the capillary is sufficiently rinsed with dilute sample solution, the solenoid valve controlling the 10 psi rinsing pressure is turned off and the Z-axis ann picks up the detector module from the working plates, the lifting mechanism still being energized. Once raised, the detector module is transported to a vial containing pure buffer solution and the inlet electrode/capillary pair is dipped into the solution by the Z-axis to remove traces of sample contaminating the external surfaces of the inlet electrode/capillary pair. After dipping, the detector module is raised, translated, and dropped again into an empty vial to catch waste buffer clinging to the surfaces of the inlet electrode capillary. Any liquid attached to the pair is blown off into the empty vial by turning on the 10 psi air normally used to create rinsing pressure in a sealed container. Since in this case, the O-ring is not brought in contact with the top of the waste vial, the air flows fairly vigorously and blows off any clinging liquid. Now the detector module having a decontaminated and dry inlet capillary/electrode is raised, translated and lowered into a sealable via), containing a solution of target molecules. The Z-arm applies pressure to the top of the vial once again, and the system turns on a solenoid valve controlling the pressure used for sample injection. When the interior of the target vial is pressurized (typically 0.5 psi for 5 sec with a 50 μm inner diameter capillary), sample is injected (typically 50 nL) up into the very beginning of the inlet capillary end. Now the Z-axis arm again lifts the detector module and returns it to the same two working plate wells containing the sample rinsed through the capillary. The lifting mechanism is released from the detector module and the arm assembly 12 is free to go begin another sample preparation step or go to move another detector module 26. Simultaneously, the high voltage is turned on and the target begins its migration to the outlet working plate well, passing through a solution containing potential ligands. Any interaction between the diluted sample buffer and the target injection liquid will cause the resulting electropherogram to deviate from the control profile where there is no potential ligand material present. At the completion of the programmed electropherogram run time, the detector module is recovered by the lifting mechanism and transferred back to the docking station where the hold-down mechanism squeezes the inlet O-ring between the underside of the detector and the top of a 4 mL buffer vial. A full vial at the outlet end of the detector washes off the outlet electrode/capillary end and catches flow coming from the capillary during the buffer rinsing operation. Now the rinsing pressure, typically 10 psi, is again turned on and a couple hundred microliters of pure buffer are rinsed through the capillary from inlet to outlet end to remove all traces of the previous sample and the target. The detector module is now available to have the next sample dilution solution rinsed through the capillary.

The two steps prior to the target injection are intended to preserve the useful life of the target reagent. The buffer dip washes sample off the electrode/capillary and prevents contamination of the target vial. The blow-off step prevents dilution of the target solution from any buffer clinging to the electrode/capillary.

Figure 6:
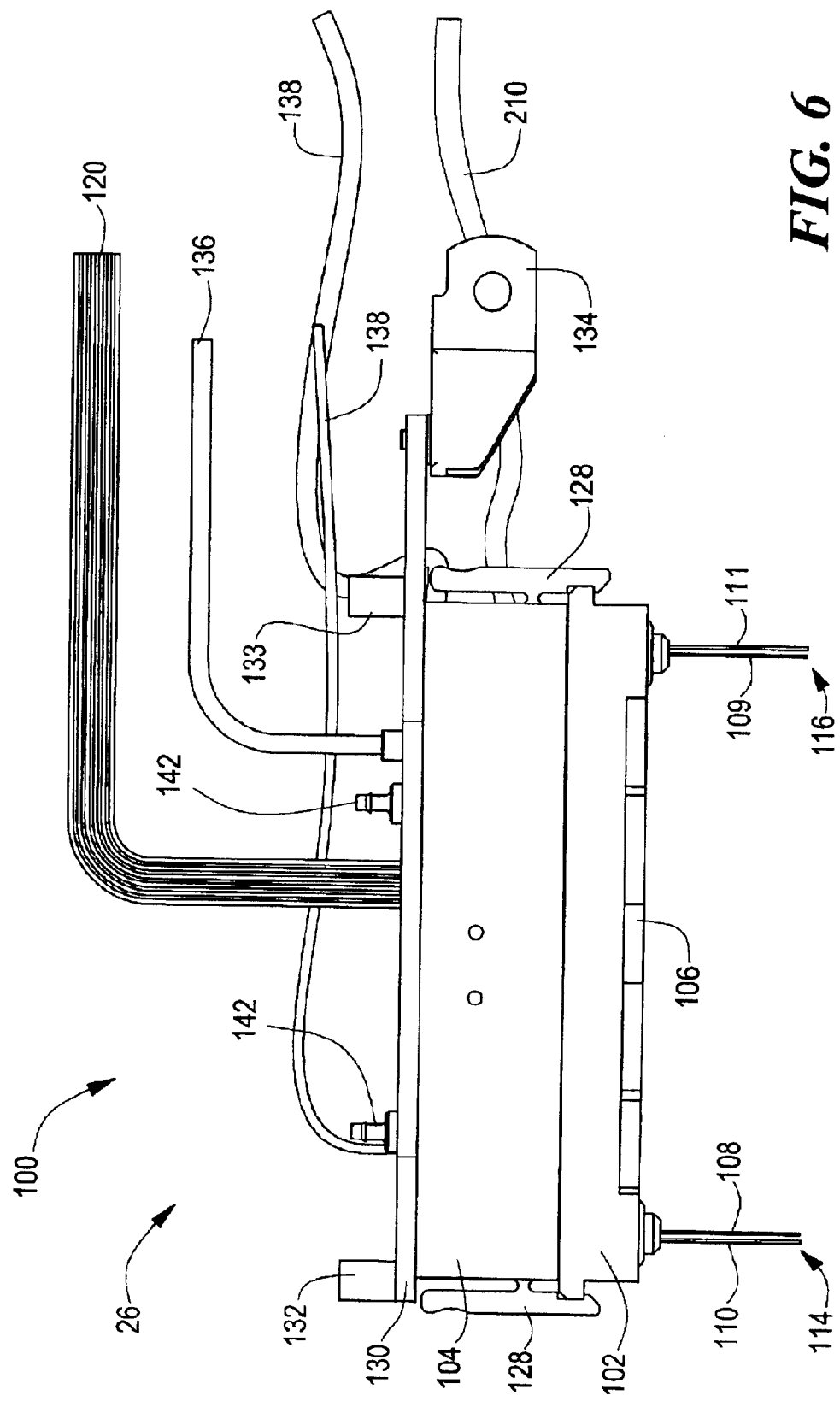
FIG. 6 is a front view of one embodiment of a detector module of the invention, specifically an ultraviolet (UV) absorbance detector.

FIGS. 6–14 illustrate a miniaturized ultraviolet (UV) detector module 100. The detector module includes a removable cartridge assembly formed with an upper housing 104 and a removable cartridge component 102. As also shown in FIG. 6, the upper housing 104 and the cartridge 102 are held together by two retaining latches 128. The detector halves may be secured by other suitable means. The cartridge 102 contains a magnetizable hold-down plate 106 on the bottom surface of the cartridge secured in any suitable manner, as by screws. This magnetizable hold-down plate 106 is activated for parking at the docking station 24. The magnetizable hold-down plate 106 also includes four cutouts or scalloped recesses 107 so that the hold down plate does not come in contact with the hold-down magnets 53 associated with an adjacent detector module position on the docking station.

Appropriate passages are available for extending an inlet capillary end 108, an inlet electrode 110, an outlet capillary end 109, and an outlet electrode 111 at the ends of the cartridge 102, with an extension of about 2.0 cm to reach near the bottom of a sample and a discharge well. The cartridge 102 has at both ends passages 140 for receiving the capillary inJ.et and the outlet. The inlet end 114 of the detector serves to position the capillary inlet 108 with a well containing any of several liquids. The outlet end 116 of the detector serves to position the capillary outlet 109 to a well for collecting the discharge during analysis and rinsing operations. Surrounding an alignment probe feature at each end of the cartridge, is an O-ring 112 sized so as to seal with the top of any vial from which one would need to rinse or inject. This would include dock vials to rinse and to initialize the capillary for the next sample, the working plates from which sample solution is rinsed through the capillary, and the target vial from which a small injection volume is forced partway up the inlet end of the capillary. Additionally, the inlet electrode 110 and the outlet electrode 111, which are aligned and in parallel with the capillary, are also extended from each end of the cartridge 102. However, the electrodes are permanently attached and electrically connected to the upper housing 104. Specifically, the inlet electrode 110 is soldered to conductor 138 and the outlet electrode 111 is soldered to conductor 138. The two electrodes slide through specific clearance holes 140 in each end of the cartridge during removal or installation.

Between the magnetizable hold-down plate 106 and the cartridge 102, a custom photodiode amplifier assembly 118 is provided which connects with the power and signal cable 120 mounted to the upper housing 104. The cartridge 102 also contains a capillary alignment channel 121 on its top center surface that runs longitudinally for holding the capillary. The cartridge 102 also contains a capillary window location 122 near the outlet end of the detector module 100 for detecting UV light variations as a sample mixture moves through the capillary window from the inlet end to the outlet end of the capillary.

Figure 12:
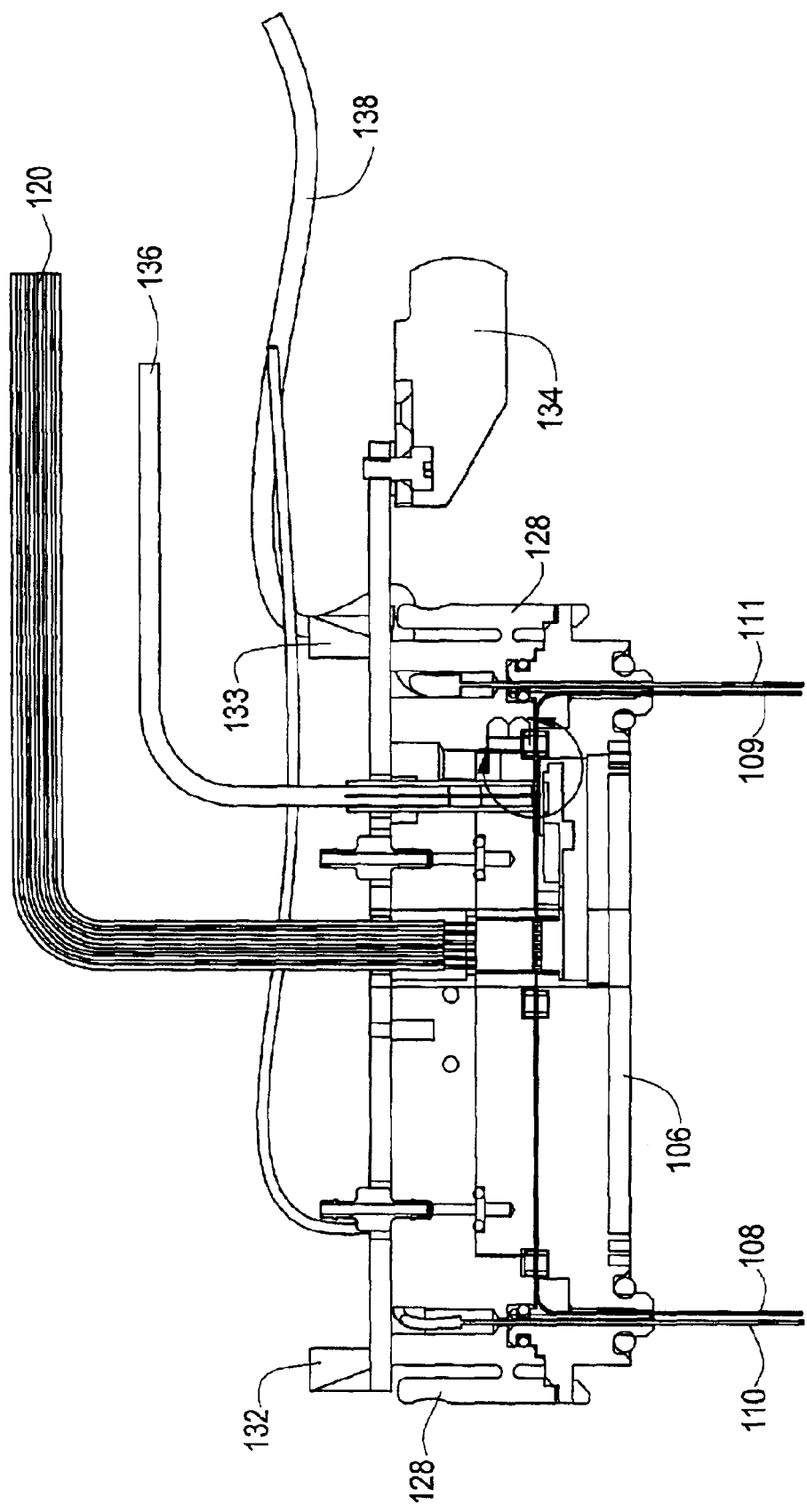
FIG. 12 is a cross-sectional view of the UV detector module along line A—A of FIG. 11A.
Figure 15:
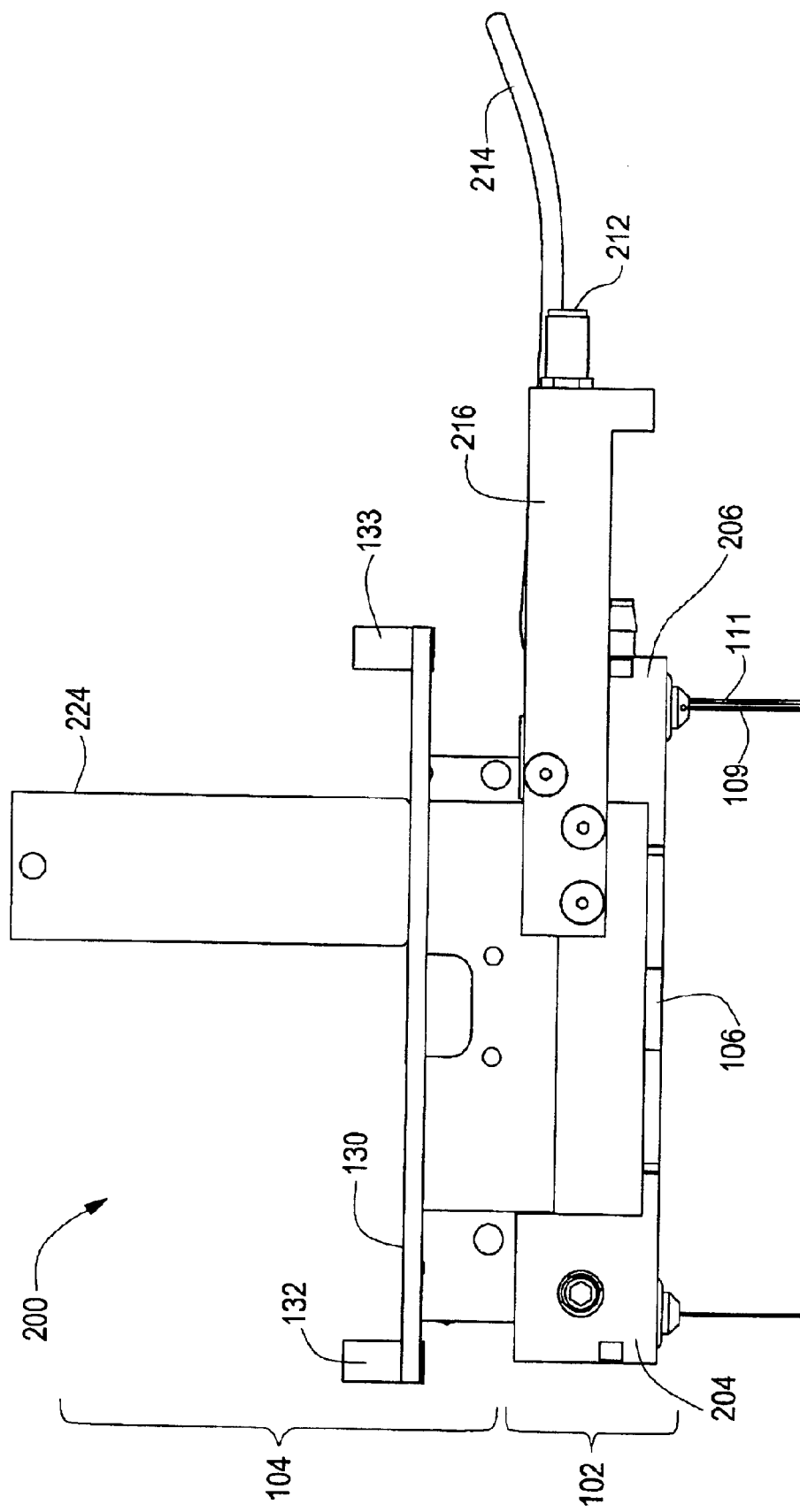
FIG. 15 is a front view of another embodiment of a detector module of the invention, specifically a laser-induced fluorescence (LIF) detector.

In between the upper housing and the cartridge is contained a heat sink 124, formed, for example, from aluminum, for absorbing heat generated by electrical current passing through the capillary due to the high voltage applied. Appropriate capillary retainers 126 are evenly spaced (as shown in FIGS. 7, 12 and 13) to hold the capillary in place in the alignment channel so that when the cartridge is pressed onto the bottom of the upper housing, the capillary will be sure to align itself with the capillary alignment channel on the bottom center surface of the heat sink that runs longitudinally for holding the capillary. The retainers 126 also serve to add rigidity to the assembled capillary so the window will not break when the cartridge is handled. The temperature of the capillary affects the consistency of the separation and the resulting electropherogram. Providing a stable environment while performing the separation must be accomplished or it becomes difficult to interpret the degree of binding that may exist. Binding of a hit is inferred from the electropherogram by assessing the magnitude of the distortion caused in the unbound target peak (separation control). The detector modules 26 are designed such that a significant length of the capillary is in contact with the heat sink 124. The heat sink 124 comprises a thermal mass containing passages through which a temperature-controlled coolant flows. In this way, the capillary, in contact with the heat sink 124, is regulated and stabilized at a temperature determined by that of the coolant.

The upper housing 104 has a first retaining latch 128 and a second retaining latch 128 on the left and right sides to tightly connect both the upper housing 104 and the cartridge 102 together. The upper housing 104 also has a magnetizable pick-up plate 130 on the top surface of the upper housing 104. The magnetizable pick-up plate 130 has a first magnetic alignment guide 132 and a second magnetic alignment guide 133 on the top side ends of the magnetizable pick-up plate 130. The magnetizable pick-up plate 130 has, at one end, a flexible cable guide connector 134 for attachment to the base of the CE system to contain the several electrical cables, the UV light source cable, and the pneumatic tubes necessary to make the detector module function. The upper housing 104 and the magnetizable pick-up plate 130 also contain corresponding passages for acceptance of various electrodes and cable guides. For example, the upper housing 104 has a power and signal cable 120 which connects through to the cartridge 102 to the custom photodiode amplifier assembly 118. The upper housing 104 also houses a fiber optic cable 136 for a UV light source and high voltage cables 138 for the electrode cable wires. Two passages are shown on the magnetic pick-up plate 130 to have access for coolant tubing to connect to a fitting 142, which provides for connection to passages internal to the upper housing 104 and to passages internal to the heat sink 124.

With regard to the interaction of the UV light source and a sample, the path length of the UV light through the sample liquid is equal to the inside diameter of the capillary. Most separations are performed in 50 $\mu$ ID capillary. This provides a light path length of 0.05 mm through the sample liquid. Prior art high performance chromatography detectors provide maximum sensitivity by using a flow cell with a 9.0 mm path length. Because the path length in the present invention is considerably shorter, the UV absorbance detector exhibits higher amplification of the photodiode signals. For example, a detector with a light path of 0.05 mm produces a light attenuation change of only $\frac{1}{180}^{th}$ as large as a flow cell with a path length of 9.0 mm. In addition, electrical and optical noise are reduced to the lowest practical limits to assure a signal-to-noise ratio that provides useful sensitivity to the sample compounds. The UV light that falls on the photodiode without passing through the absorbing sample liquid contains no absorbance information and is eliminated or substantially eliminated. To measure UV light attenuation, the fiber optic source, the capillary window, and the photodiode are aligned sufficiently to capture all the information-rich attenuated light that has passed through the liquid and to prevent any light from falling on the photodiode that has not passed through the sample liquid.

Figure 7B:
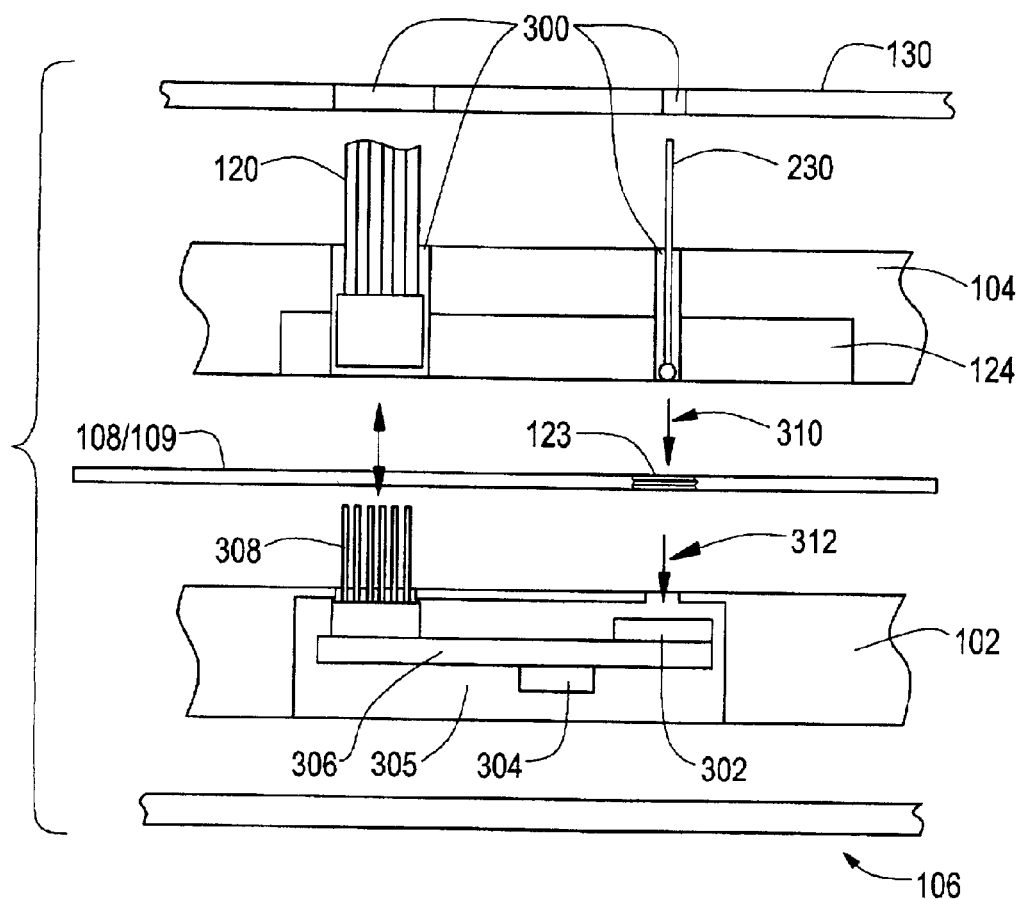
FIG. 7B is an exploded view of the photodiode/amplifier assembly of FIG. 7A.

Referring more particularly to FIG. 7B of the photodiode amplifier assembly, a UV source is provided in communication with a fiber optic cable 230 disposed through appropriate through holes 300 in the housing 104 and magnetizable pick-up plate 130. Preferably, a deuterium source lamp is used to generate a broad range of UV wavelengths 310 from which to select. Preferably, an interference filter (not shown) is placed between the source lamp and the inlet end of the fiber optic cable 230 to select a single wavelength to be monitored. Typically, a UV absorbance detection is optimally performed at one of three distinct wavelengths: 214 nm, 256 nm, and 280 nm. The outlet end of the fiber optic cable is mounted rigidly against the capillary window 123 to accurately direct the maximum amount of emitted light possible through the sample liquid in the capillary. Directly opposite the fiber 230, on the other side of the capillary, a silicon photodiode 302 is mounted so that the UV light 312 emanating from the sample liquid falls on its photo-sensitive surface. The extremely small variations in photocurrent produced by the changing UV intensity striking the photodiode are amplified by a precision low noise/high gain amplifier integrated circuit 304 mounted immediately opposite the diode on a small printed circuit board 306.

To prevent any external electrical interference from increasing the baseline noise of the photodiode/amplifier assembly, the photodiode chip 302 and the amplifier circuit 304 are fully embedded in a cavity 305 inside the cartridge. The cavity is preferably treated with conductive paint to shield the sensitive circuitry. In this manner, the electrical noise level may be kept low to maximize the signal-to-noise performance of the detector. A connector 308 is provided on the circuit board 306 to deliver power to the amplifier 304 and to deliver the amplified absorbance signal to the data acquisition system. The connector 308 allows the cartridge to be removed from the upper housing to replace the capillary.

In operation of the detector modules, the arm assembly engages its magnetic solenoids to a detector module thereby energizing the magnetic plate of the detector for pick up. The arm assembly precisely transports the detector to an appropriate inlet and outlet vial pair where a sample is already prepared for analysis. The detector is lowered such that the capillary/electrode inlet immerses into, for example, a 5 $\mu$l volume of sample liquid. In the dilution method described previously above, the pipette adds about 200 uL to the original sample or control well, mixes it, and then dispenses matching 100 uL volumes to each working plate well. This is sufficient volume to assure that the capillary inlet end and the electrode will be immersed when the detector module is placed on top of the working plate array. The rubber O-ring located on the bottom of the detector module provides a seal against the opening of the target vial, the inlet working plate, and the inlet docking vial. The detector module applies an injection pressure to the target vial and transfers an injection volume of target into the inlet end of the capillary. The arm assembly disengages from the detector module magnetic pick up plate to continue with another preparation and analysis using another detector module or to use the pipette to prepare another sample. A high electric voltage is applied to migrate the target through the capillary and past the window for analysis in accordance with customary analytical methods. As the target flows through the capillary and passes the detection window, a photodiode detector/amplifier sends an analog voltage to a sensing board in the controlling computer that represents the reading of the analysis. Preferably, it is displayed as an analog waveform on a display device in real time. The target liquid then flows out from the capillary outlet end and into a discharge well as waste.

Referring more particularly to FIGS. 15–25B regarding the miniaturized CE laser-induced fluorescence (LIF) detector module 200, the LIF detector assembly contains an upper housing 104 and a removable cartridge 102 held together in any suitable manner, as by screws. The cartridge 102 contains a magnetizable hold-down plate 106 at the bottom surface of the cartridge. The magnetizable hold-down plate 106 is scalloped (107) to avoid contacting the magnets 53 in adjacent docking positions on the docking station 24 (see also FIGS. 18, 22 and 23). Similarly, this magnetizable hold-down plate 106 when pulled downward by the force of the magnets 53 in the docking station, provides sealing pressure to the inlet O-ring so that rinse operations can be performed upon the capillary without tying up the Z-arm by having it press on the top plate of the detector module in the same manner as it must in the case of rinsing the capillary with solution contained in a working plate well. In addition, the magnetic hold-down plate extends outwardly from both sides of the bottom of the detector module in order to add stability to the free standing detector module when it has been placed on the working plate array. The working plates lack the electromagnets to securely hold the detector stationary after the Z-arm releases the module.

Figure 23:
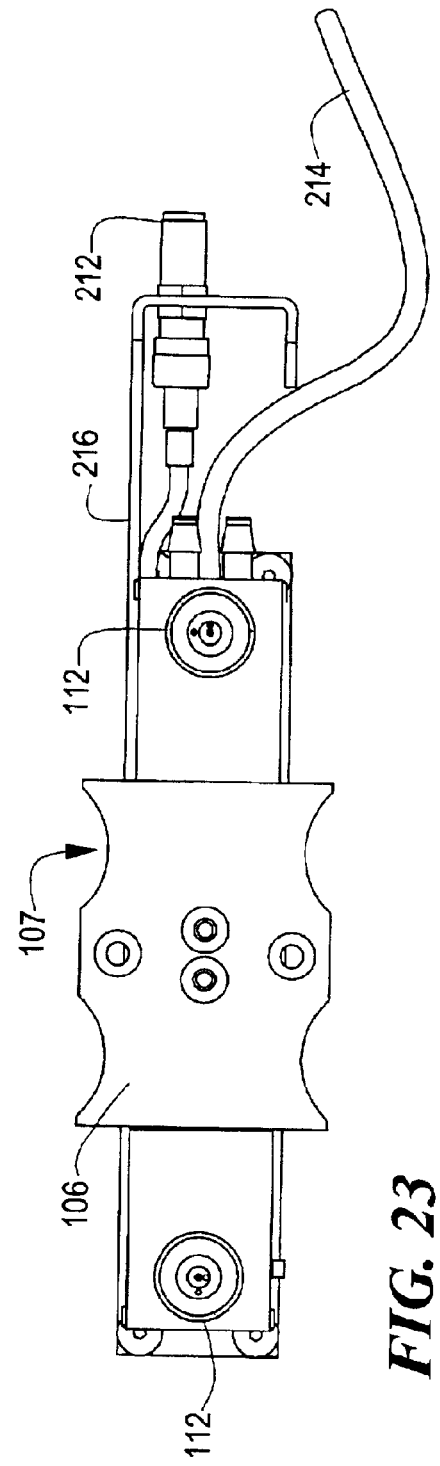
FIG. 23 is a bottom view of the LIF detector module of FIG. 15.

The cartridge 102 of the LIF detector also contains a longitudinal capillary alignment corner on its top center surface. An area 203 on the cartridge which houses the capillary window for separation detection is specially grooved to minimize detection of background energy as further discussed below. The inlet end 114 of the detector module serves to position a capillary inlet 108 and an associated electrode 110 with a reservoir containing a sample to be analyzed or any number of other liquid containing or empty containers depending upon the requirements of the analysis. The outlet end 116 of the detector serves to position a capillary outlet 109 and an associated electrode 111 to a reservoir for collecting any liquid flowing from the capillary outlet either during sample preparation steps, during the assay, or during post-run capillary rinsing steps. At both the inlet and outlet ends of the detector module, O-rings 112 (as shown in FIG. 23) surround the tapered well alignment probe from which the capillary and electrode extend. The O-rings 112 serve to make a seal between the working wells and any other container where it is necessary to force the solution through the capillary with pneumatic pressure. When liquid flow is desired, either the Z-arm or the docking station pull-down magnets squeeze the O-ring between the bottom of the detector module and the top of the solution container. Turning on the pneumatic solenoid valve for either rinsing pressure (for example 10 psi) or injection pressure (for example 0.5 psi) pressurizes the container and forces the solution into the capillary because the outlet end of the capillary is at atmospheric pressure.

Figure 18:
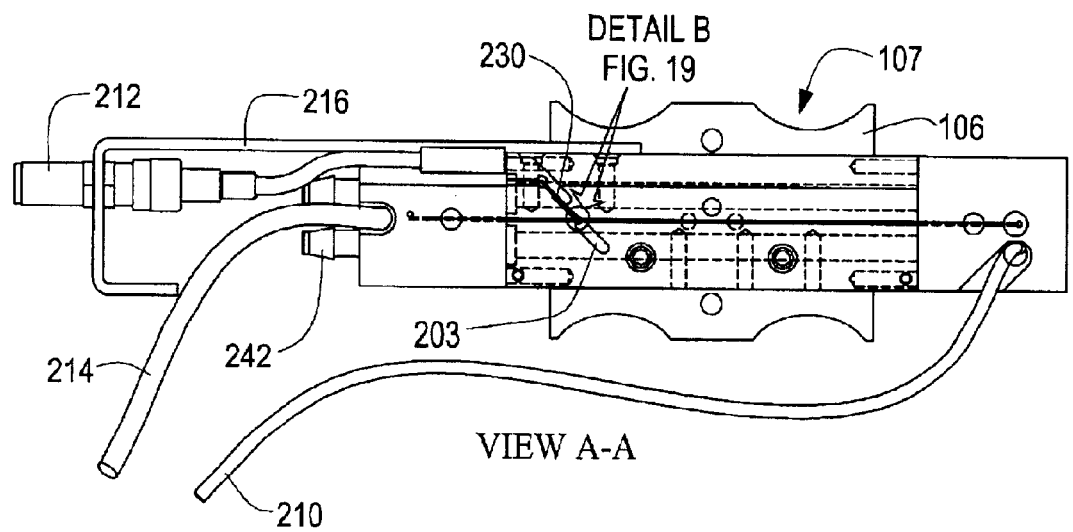
FIG. 18 is a top view of the cartridge of the LIF detector of FIG. 15.

The cartridge 102 of the detector module includes a first end block 204 where a capillary inlet end 108 and its associated first electrode 110 extends out from the inlet end 114 of the detector module. The cartridge also provides a second end block 206 for a capillary outlet end 109 and its associated second electrode 111, which extends out from the outlet end 116 of the detector module. Various ports are made available in the cartridge through the end blocks. The end block 204 containing the inlet portion of the capillary and the electrode has a through hole 240 to accommodate a pneumatic connection 241 (FIG. 24) for the rinse and inject pressure. The end block 206 containing the outlet portion of the capillary and the electrode provides a barbed connector 242 for connecting tubing for the coolant supply that flows through the cartridge. The outlet end of the detector module provides attachment for a metal support 216 (FIGS. 16A and 18) for connecting the cable guides 25, which retains the cabling from various sources to prevent tangling and ease of movement of the detector modules. This metal support 216 also provides mounting for the fiber optic connector 212 (as shown in FIG. 18) used to supply excitation laser light to the optical fiber segment permanently irnbedded in the cartridge with epoxy.

Figure 19:
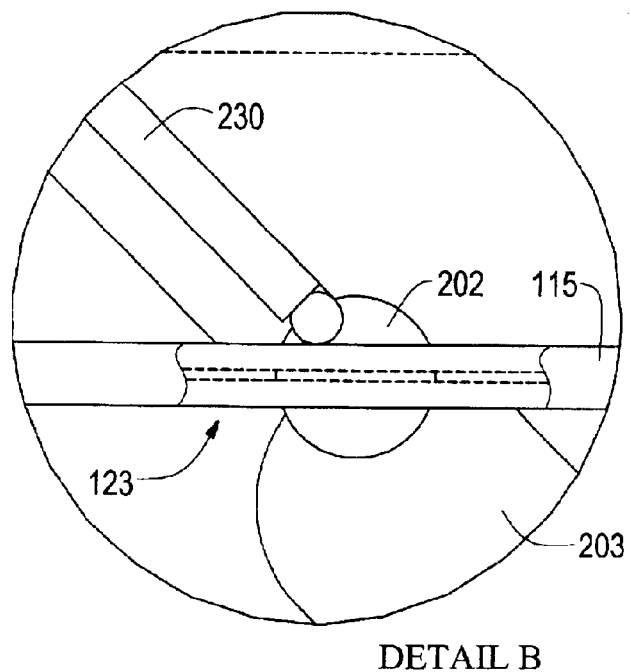
FIG. 19 is a partial view of the Detail B of FIG. 18, which shows the angular placement of the fiber optic cable with respect to the capillary, which also depicts the hole and relief made in cartridge to reduce the background energy of the laser light source to the photomultiplier tube (PMT) assembly.
Figure 20B:
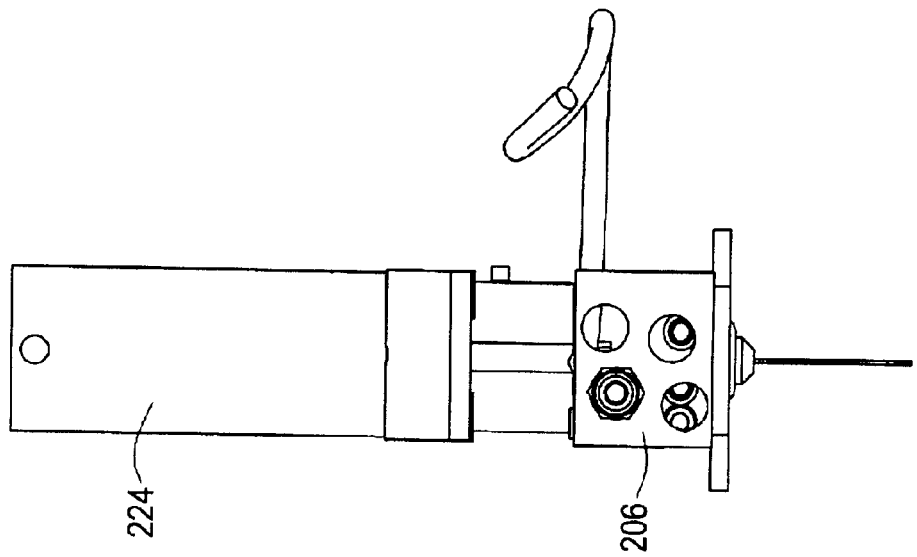
FIG. 20B is a right side view of the LIP detector module of FIG. 15.
Figure 20A:
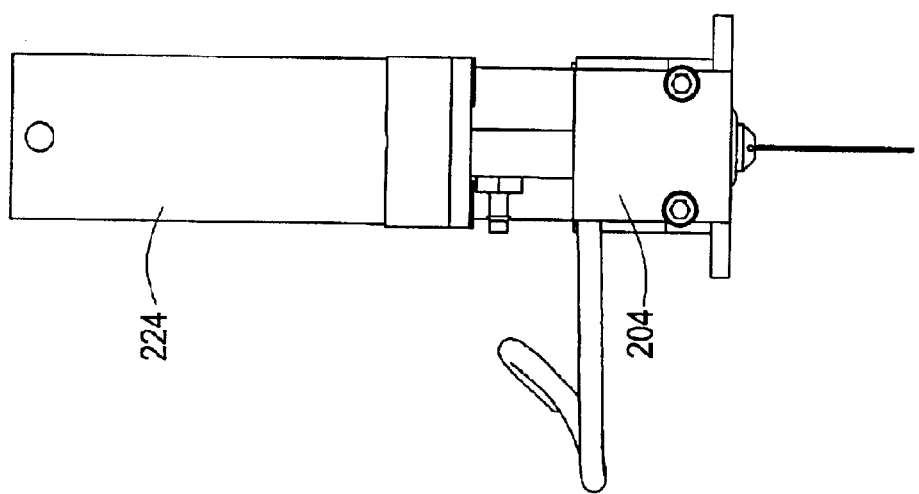
FIG. 20A is a left side view of the LIF detector module of FIG. 15.
Figure 21:
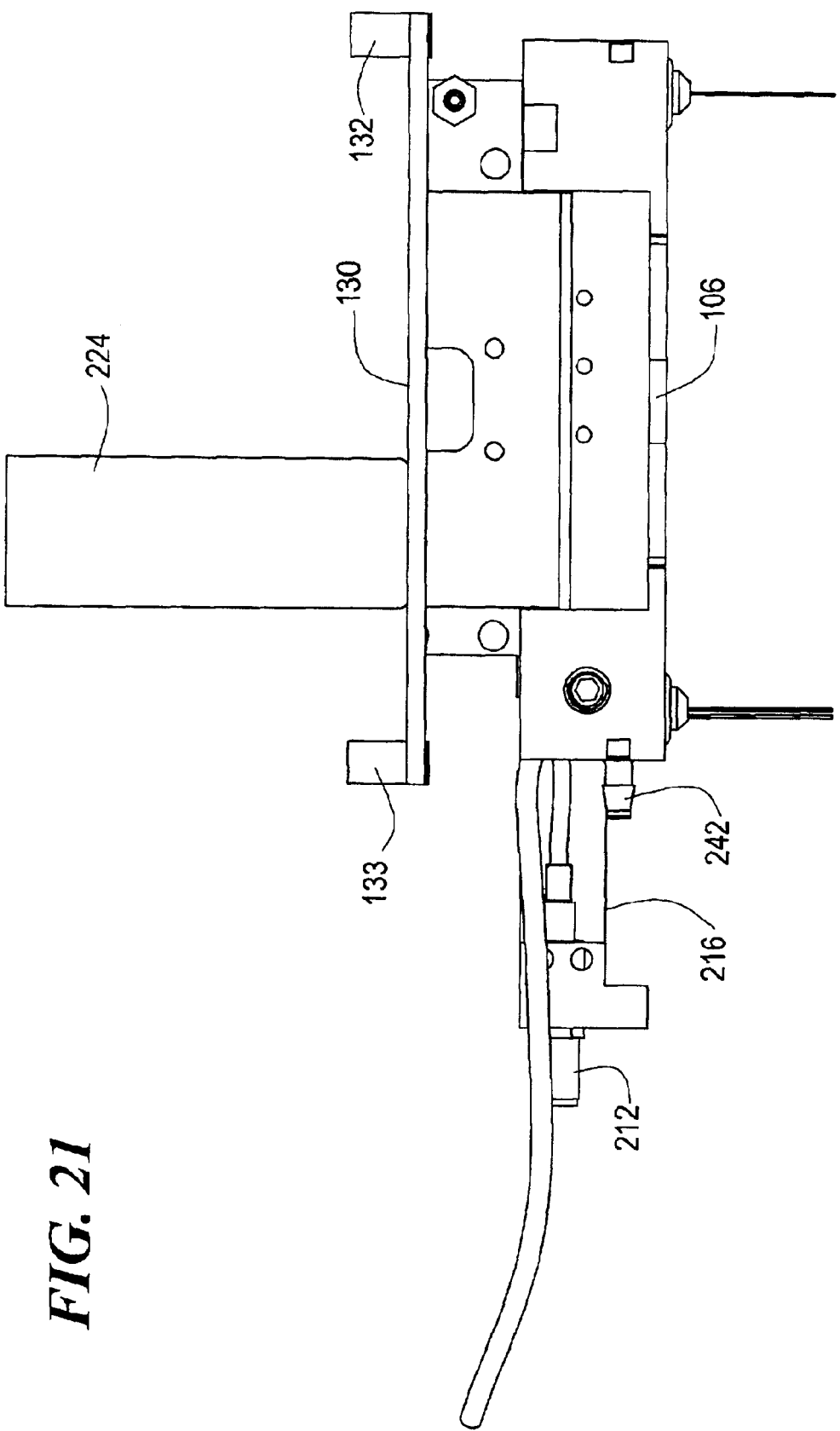
FIG. 21 is a back view of the LIF detector module of FIG. 15.
Figure 22:
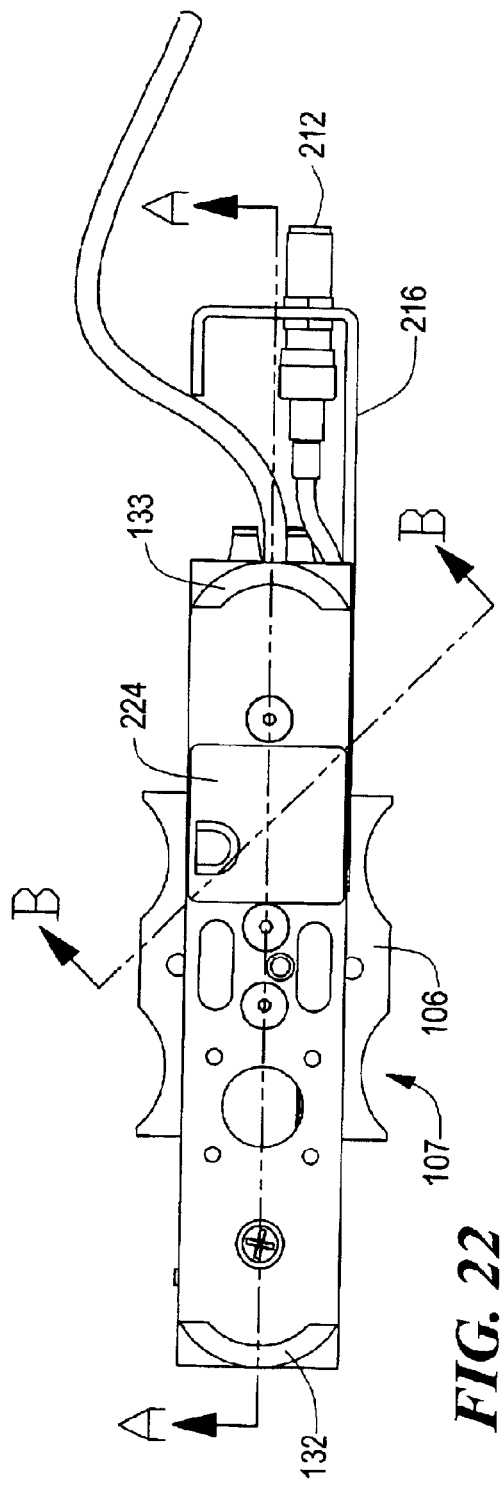
FIG. 22 is a top view of the LIF detector module of FIG. 15.

A clamping plate 218 (FIG. 16A) is affixedly aligned on top of the cartridge 102 to cover the capillary 108/109 and the laser light source 230 (FIG. 19). On the underside of clamping plate 218, a second corner is provided to capture the capillary between the corner on the top surface of the cartridge 102 and the corner on the underside of the clamping plate 218. The capillary is rigidly secured between the two corners when the clamping plate is screwed onto the top of the cartridge. The clamping plate 218 has a convenient hole 220 to allow for the fluorescent light from the capillary window to pass through to the photomultiplier tube (PMT) for separation detection.

In between the cover plate 218 and the upper housing 104, an optics assembly 222 is positioned accordingly above the capillary window and below the PMT to maximize the fluorescent light (the signal) and to minimize the amount of excitation light (input laser) which reaches the PMT for detection. In contact (tangent) with the top surface of the capillary 115, immediately below the microscope objective lens, is an optical mask to block scattered background excitation light from entering the lens and reaching the PMT. The width of the slot in the mask is calculated to allow only 116 degree solid angle of light required by the microscope objective. For a given 488 nm intensity level on the capillary window, the intensity of 520 nm light emitted from the window is proportional to the amount of labeled target present. The pattern of 520 nm light emitted from the window is essentially spherical due to the randomness of photon emission as excited electrons decay back to their lower level in the fluoroscine molecule. To maximize the signal-to-noise level of the detector, the detector should collect the maximum solid angle of 520 nm emitted light possible, but minimize the amount of 488 nm excitation energy collected. Accordingly, a high numerical aperture lens is used to collect the maximum amount of fluorescent light possible. Similarly, the excitation light axis and the axis of the collection optics are preferably orthogonal. Interference filters are optimized for light passing through normal to the surface.

Figure 16A:
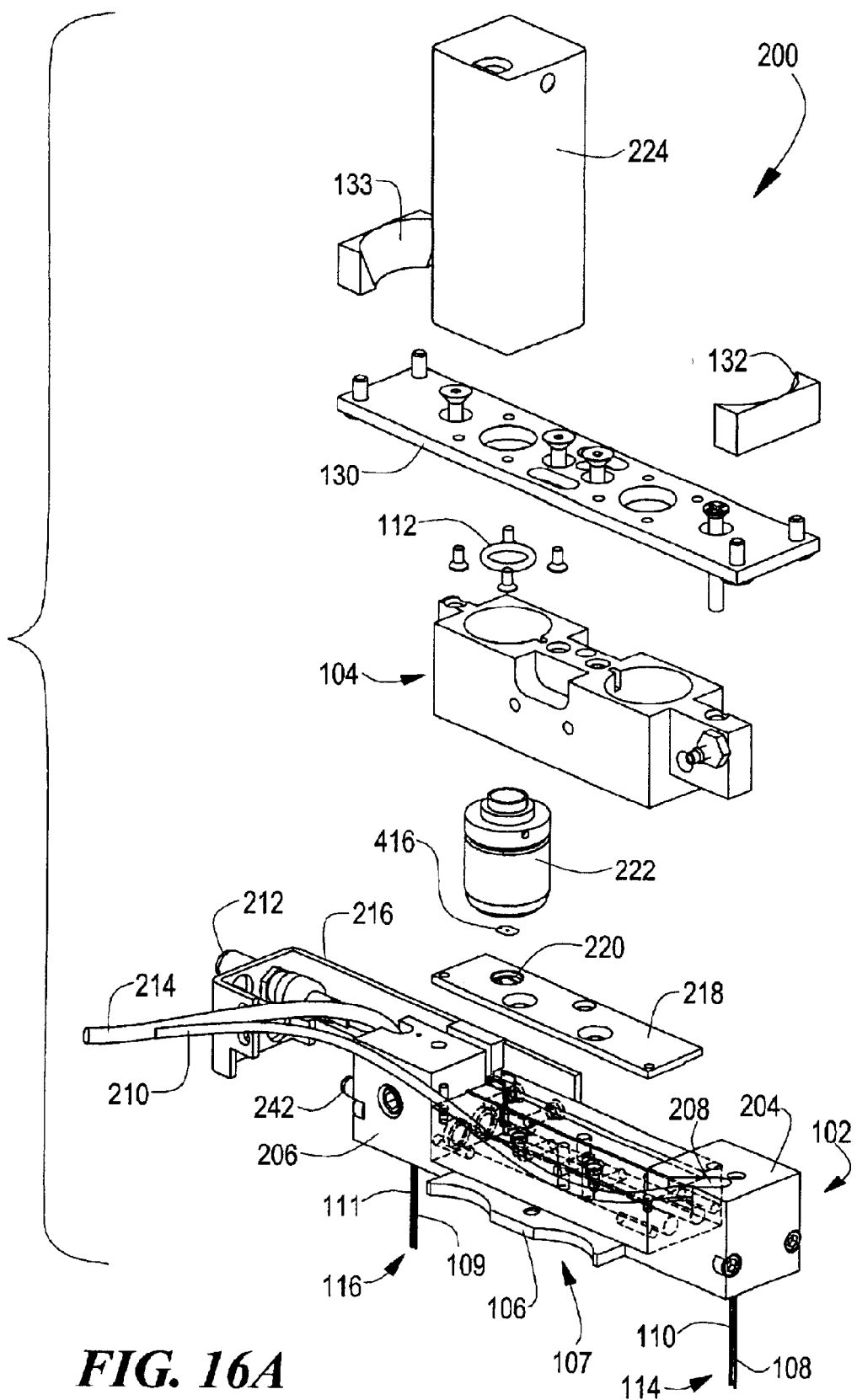
FIG. 16A is an exploded isometric view of the LIF detector module of FIG. 15.
Figure 16B:
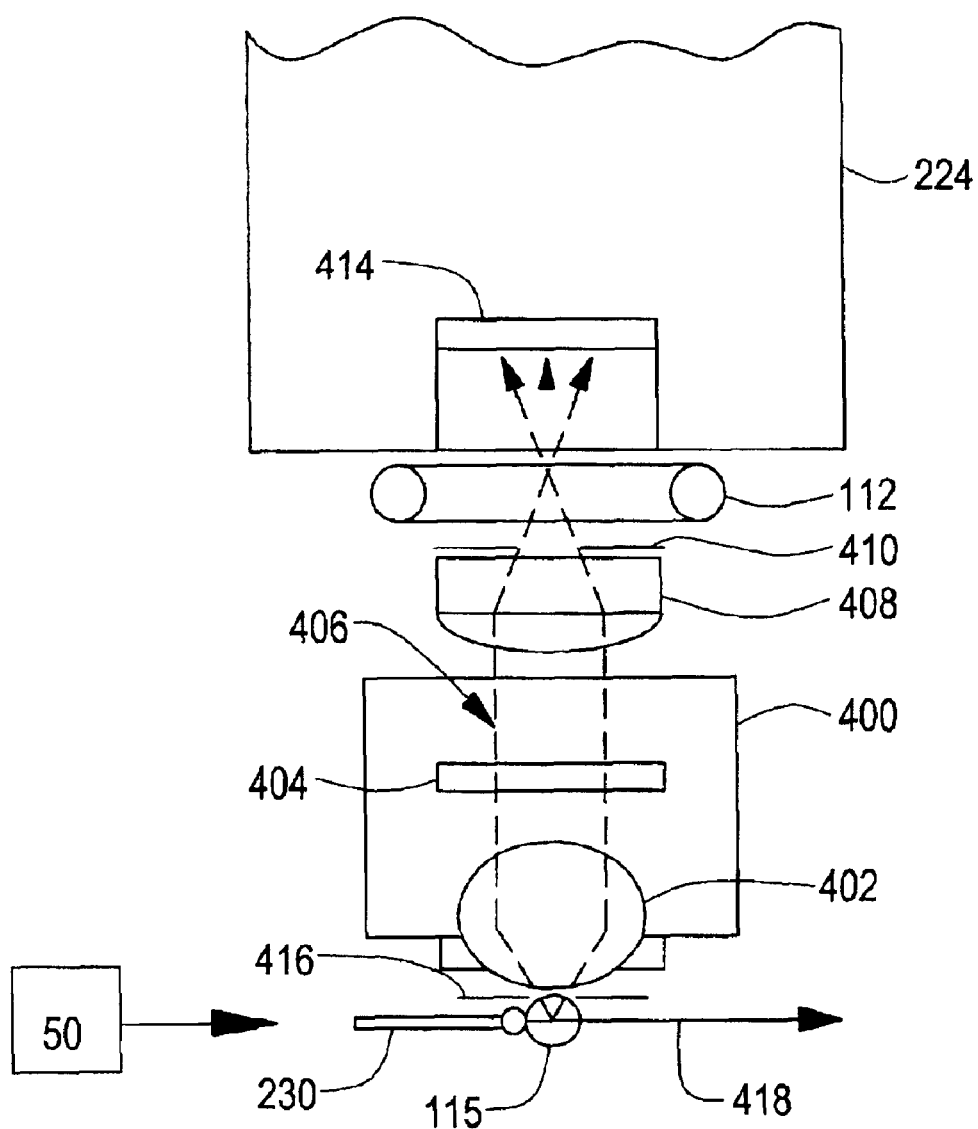
FIG. 16B is an exploded view of the optics assembly of the LIF detector module of FIG. 15.
Figure 17:
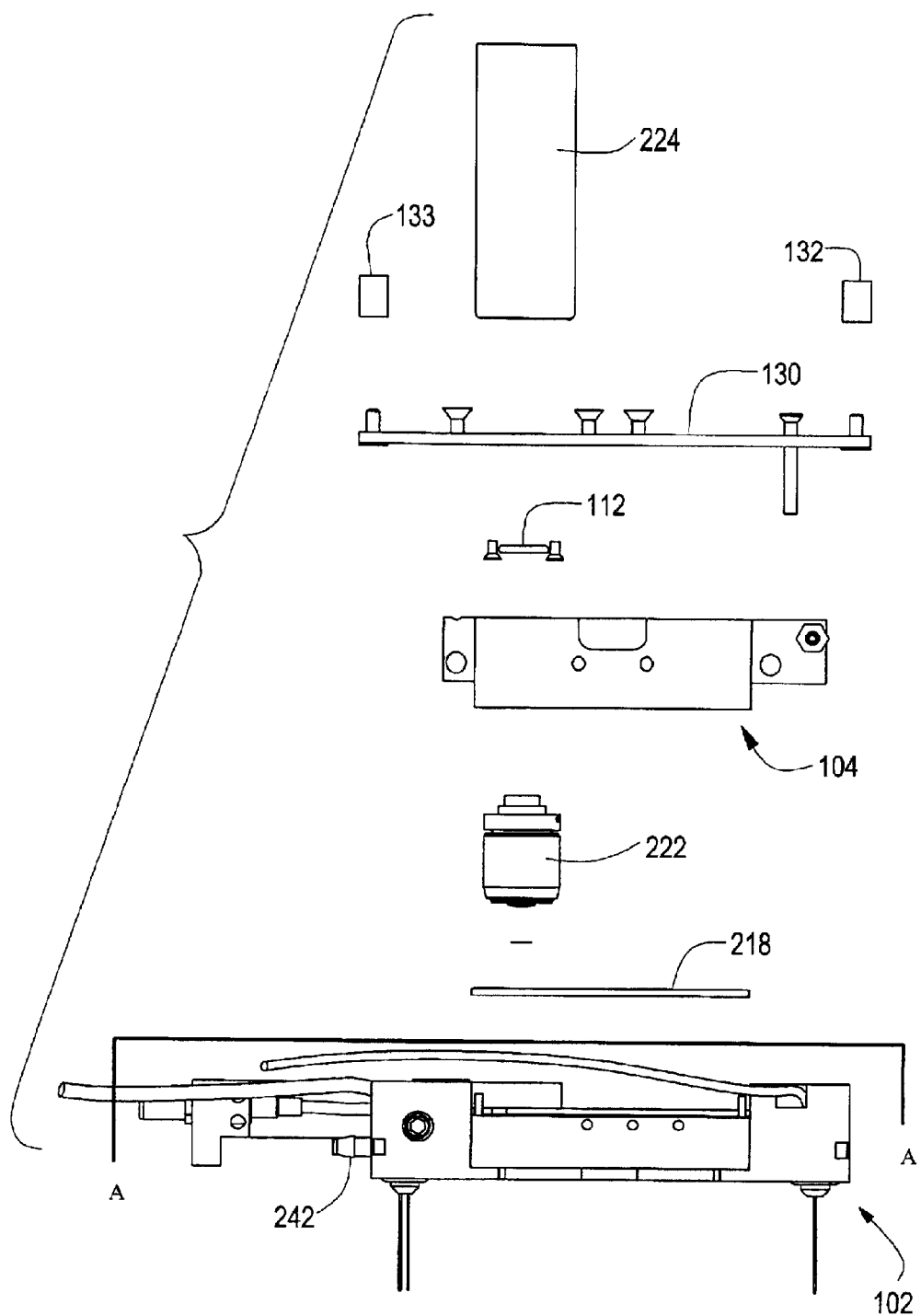
FIG. 17 is an exploded rear view of the LIF detector module of FIG. 15.

Referring to FIG. 16B, a source 50 of 488 nm light is directed onto the inlet of the fiber optic segment 230, which is affixed, as with an adhesive such as epoxy, into the cartridge 102 of the LIF detector. In this embodiment, the source is an Argon-Ion laser with appropriate outlet optics to deliver the laser energy into the fiber optic cable. The fiber optic segment is mounted such that the light strikes the capillary window 123 at a non-90 degree angle to minimize reflections of excitation energy into the PMT detector 224. Most of the 488 nm excitation energy exits along path 418.

A capillary mask 416 to block background excitation light is provided above the window 123. A microscope objective lens assembly 400 is provided above the mask 416. The objective lens assembly is selected for high magnification, which translates to high numerical aperture, or preferably N.A. 0.85. The higher the N.A. of an optical element, the larger is the angle over which light passes into or out of the device. In the case of the 63X objective lens 402 used in this embodiment, the N.A. calculation shows that light within a 116 degree solid angle emitted by the fluorescing liquid in the capillary will be collected by the microscope lens. The liquid in the capillary is located at a working distance away from the front lens surface of the objective so that any light emanating from the liquid exit the lens inside the objective in parallel rays. Conversely, light entering the lens from any point other than the center of the capillary will not travel in a line parallel to the axis of the objective lens assembly. These parallel light rays pass through a high-pass optical interference filter 404 that is intended to block the 488 nm excitation energy, but allow the 520 nm fluorescent energy to pass through with minimal transmission losses. This type of filter requires that light to be filtered pass through the filter on a ray 406 at virtually 90 degrees to the surface of the filter. The inside of the microscope objective is modified to accommodate and hold securely the filter in a plane 90 degrees to the axis of the objective. In this arrangement, because only light from the sample liquid travels through the objective on rays parallel to the axis, (the optimum performance angle), the 488 nm component of light from the liquid is expected to be attenuated by almost six orders of magnitude. Conversely, the 520 nm light passing through the filter on a ray normal to the surface is only attenuated by about 5%. After the filter in the light path, plano-convex focusing lens 408 is disposed to create a virtual image of the capillary lumen from the paralleL rays traveling through the filter a distance beyond the lens equal to the focal length of the lens. The virtual image is essentially a reconstruction of the capillary lumen in a plane behind the lens from the side where the parallel light enters. To further block extraneous light rays from striking the PMT sensor, a circular mask 410 is installed behind the plano-convex lens with a center hole diameter selected to allow only light rays coming from the center of the capillary to be focused through the hole. A light-blocking O-ring 112 is also disposed between the mask 410 and the detector 224. Rays from scattered light or other sources are thus not able to pass through the mask behind the lens. This optical design eliminates scattered rays from striking the PMT, minimizes the level of background light and maximizes the signal-to-noise of the arrangement. Finally, the light exits the mask and passes through to the PMT sensor 414. In a further embodiment, to eliminate even more background light, a pinhole mask (not shown) is placed at the plane of the virtual image, between the circular mask and the PMT sensor. This pinhole mask must be carefully aligned, or the signal energy is clipped by the mask as well and the ratio of signal-to-noise actually drops. Accordingly, the pinhole mask may be omitted if desired.

The upper housing 104 holds a magnetic pick-up plate 130 on its top surface. The removable cartridge 102 has passages available for the light coming from the capillary window 123 (FIG. 19) to reach the PMT 224 for detection. An O-ring 112 is fitted in between the upper housing 104 and the magnetizable pick-up plate 130 to seal out any ambient light, which may leak into the PMT light sensor. A first magnetic alignment guide 132 and a second magnetic alignment guide 133 are positioned at both ends on top of the magnetic pick-up plate 130. The guides 132 and 133 are provided to exactly position the pick-up magnets on the Z-arm on the pick-up plate when securing a detector module for transport. Realignment of the detector module relative to the Z-arm is necessary on each manipulation to maintain the accuracy required to insert the electrode/capillary into the small well opening reliably. The PMT assembly 224 is positioned on top of the magnetic pick-up plate 130, which is aligned to the capillary window for detection. More than one PMT assembly may be attached to the LIF detector depending on the type of analysis. For example, a single capillary can be fabricated with two viewing windows such that an "early" and a "late" signal can be produced from a single analysis separation event. The early and late detector signals comparatively can be interpreted to reveal difficult-to-obtain kinetics information about the binding properties between potential therapeutic drug targets and various ligands including unknown molecules present in the extracts of natural samples, synthetic compounds, and combinatorial mixtures.

Figure 25A:
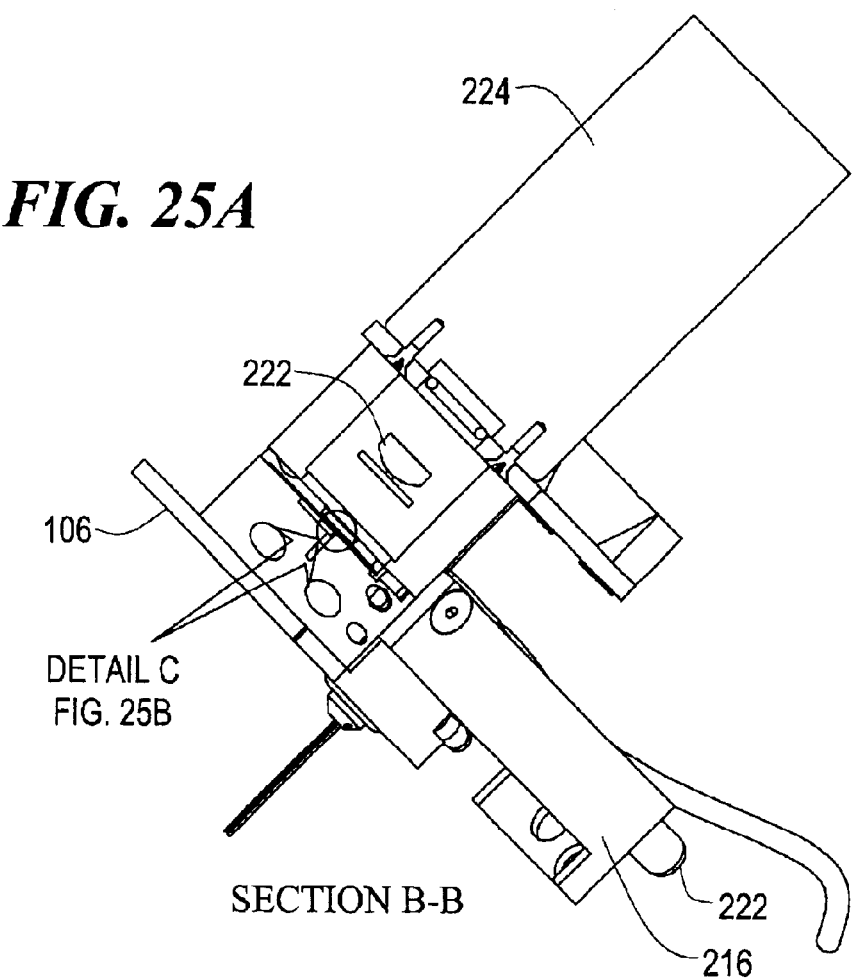
FIG. 25A is a cross-sectional view along line B—B of FIG. 22.
Figure 25B:
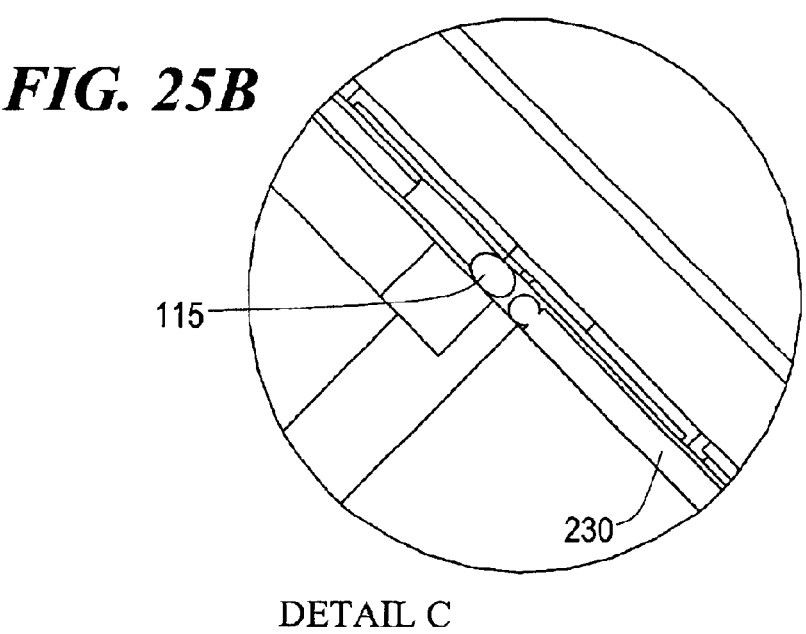
FIG. 25B is a partial view of Detail C of FIG. 25A, depicting a cross-section of the fiber optic cable with respect to a cross-section of a capillary.

In FIG. 18, a top view of the cartridge 102 reveals an angular placement of an optical fiber segment 230. Deliverance of the excitation energy by the fiber optic cable through the fiber optic connection to the X-axis of the capillary lumen at some non-90° angle (as shown in detail in FIG. 19) virtually eliminates the excitation wavelengths from the axis from which the fluorescent energy is being detected. The angle is preferably as small as possible without reaching the critical angle, at which light is reflected and does not enter the fluid in the capillary. A 45 degree angle has been found to be suitable. Eliminating the excitation component reduces the amount of detectable background energy and increases the signal to noise ratio of the detector. The optical fiber supplying the laser light is closely placed next to the capillary window as shown in FIG. 25.

In operation, the LIF detector module is interfaced substantially the same way as the UV detector module in the CE system.

In an alternative embodiment, the electrodes associated with the inlet and outlet capillary may be disposed on the docking station for alignment with the capillary during an analysis.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A capillary electrophoresis system comprising:
   a base;
   a plurality of wells disposed on the base;
   an arm assembly mounted to the base and movable in three dimensions;
   a detector docking station mounted to the base; and
   a detector module comprising a capillary extending from an inlet end to an outlet end, a pair of electrodes extending adjacent the capillary inlet end and the capillary outlet end, and a detector aligned with a portion of the capillary, the arm assembly operative to move the detector module from the detector docking station to a working position with the capillary inlet end and an associated electrode disposed in a selected well and the capillary outlet end and an associated electrode disposed in a corresponding selected well.

2. The system of claim 1, wherein said detector is an ultraviolet absorbance detector.

3. The system of claim 1, wherein said detector is a laser-induced fluorescence detector.

4. The system of claim 1 further comprising a microfluidic pipette mounted to the arm assembly for movement therewith.

5. The system of claim 4, further comprising a pipette wash station mounted on the base.

6. The system of claim 4, wherein the arm assembly is operative to move said microfluidic pipette to perform a sample preparation without affecting a running capillary electrophoresis analysis.

7. The system of claim 1, further comprising additional detector modules, each detector module comprising a capillary extending from an inlet end to an outlet end, a pair of electrodes extending adjacent the capillary inlet end and the capillary outlet end, and a detector aligned with a portion of the capillary.

8. The system of claim 7, wherein the arm assembly is operative to move each of the additional of detector modules individually from the detector docking station to a working position with the capillary inlet and an associated electrode disposed in a selected well and the capillary outlet end and an associated electrode disposed in a corresponding selected well.

9. The system of claim 1, wherein the capillary of the detector module comprises a glass tubing having an external polyimide coating thereon, the glass tubing free of the polyimide coating in a location to form a window at the portion of the capillary in alignment with the detector.

10. The system of claim 1, wherein the detector module further includes an upper housing and a cartridge component, the cartridge component removably attached to the upper housing, a channel is formed in the removable cartridge component, and the capillary is laid in the channel.

11. The system of claim 10, wherein the detector module further comprises a latch mechanism configured to retain the removable cartridge component to the upper housing.

12. The system of claim 1, further comprising an attachment mechanism configured to removably attach the detector module to the base.

13. The system of claim 12, wherein the attachment mechanism comprises a magnetizable element on the bottom of the detector module.

14. The system of claim 13, wherein the detector module includes a second magnetizable element on the bottom, and the retaining mechanism comprises an energizable magnetic assembly on the docking station operative to engage the magnetizable element on the bottom of the detector module.

15. The system of claim 1, wherein the detector module further comprises a pneumatic sealing element at the inlet end and at the outlet end operative to seal a respective capillary and associated electrode to a working well.

16. The system of claim 1, wherein the detector module further includes a temperature regulating mechanism operative to maintain the capillary at a selected temperature.

17. The system of claim 16, wherein the temperature regulating mechanism comprises a heat sink.

18. The system of claim 16, wherein the temperature regulating mechanism comprises a cooling channel formed in a portion of the detector module, a coolant circulatable through the cooling channel.

19. The system of claim 1, wherein the plurality of wells is disposed on a plurality of microtiter plates.

20. The system of claim 19, wherein at least one of the plurality of microtiter plates comprises a control plate, and a plurality of wells containing control samples are provided on the control plate.

21. The system of claim 19, wherein at least one of the plurality of microtite plates comprises a sample plate, and a portion of the plurality of wells containing unidentified samples are provided on the sample plate.

22. The system of claim 19, wherein at least one of the plurality of microtiter plates comprises an inlet working plate and the arm assembly is operative to fill the wells on the inlet working plate with an aliquot of sample.

23. The system of claim 19, wherein at least one of the plurality of microtiter plates comprises an outlet working plate and the wells on the outlet working plate are disposed to receive an aliquot of sample.

24. The system of claim 19, wherein at least one of the plurality of microtiter plates comprises an inlet working plate, the selected well disposed on the inlet working plate, and at least a second of the plurality of microtiter plates comprises an outlet working plate, the corresponding selected well disposed on the outlet working plate.

25. The system of claim 24, wherein the inlet working plate and the outlet working plate are configured with a selected spacing between the selected well and the corresponding selected well, and the detector module is configured with a spacing between the capillary inlet end and the capillary outlet end to allow registration with the selected spacing between the selected well and the corresponding selected well.

26. The system of claim 1, wherein the arm assembly comprises:
an X-arm extendable horizontally over the plurality of wells;
a Y-arm fixedly mounted to the base and extending horizontally along a side of the wells orthogonal to the X-arm, the Y-arm linearly movably mounted on the X-arm;
a Z-arm extending vertically, the Z-arm linearly movably mounted on the Y-arm; and
a pick-up assembly movably mounted on the Z-arm for vertical motion.

27. The system of claim 26, further comprising a track mechanism disposed on the X-arm, the Y-arm movably mounted to travel along the track mechanism of the X-arm.

28. The system of claim 26, further comprising a track mechanism disposed on the Y-arm, the Z-arm movably mounted to travel along the track mechanism of the Y-arm.

29. The system of claim 26, further comprising a track mechanism disposed on the Z-arm, the pick-up assembly movably mounted to travel on the track mechanism of the Z-arm.

30. The system of claim 1, wherein the arm assembly comprises a pick-up assembly configured to engage and retain the detector module to transport the detector module.

31. The system of claim 30, wherein the pick-up assembly includes a detector module retaining mechanism.

32. The system of claim 31, wherein the detector module includes a magnetizable element, and the retaining mechanism comprises an energizable magnetic assembly operative to engage the magnetizable element on the detector module.

33. The system of claim 32, wherein the magnetizable element comprises a steel plate.

34. The system of claim 32, wherein the detector module includes a guide member for directing the magnetic assembly of the pick-up assembly to the magnetizable element.

35. The system of claim 1, wherein the detector docking station further comprises at least a pair of wells in registration with the capillary inlet end and the capillary outlet end to receive the capillary and the associated electrode extending from the inlet end and the capillary and the associated electrode extending from the outlet end.

36. The system of claim 35, wherein a buffer solution is disposed in the pair of wells on the detector docking station.

37. The system of claim 1, wherein the detector docking station further comprises a detector module hold-down mechanism.

38. The system of claim 37, wherein the detector docking station includes a magnetizable element, and the hold-down mechanism comprises an energizable magnetic assembly operative to engage the magnetizable element on the detector module.

39. The system of claim 1, further comprising a controller assembly in communication with the arm assembly and operative to direct the arm assembly to move a selected one of the plurality of detector modules to a selected position.

40. The system of claim 39, wherein the controller assembly further comprises a display device and an operator input device.

41. A method of establishing high throughput capillary electrophoresis analysis, said method comprising the steps of:
providing the system of claim 1;
providing a sample for analysis; and
performing a capillary electrophoresis assay using the system of claim 1.

42. The system of claim 1, further comprising flexible cabling between the base and the detector module.

43. A detector module for cooperation with a capillary electrophoresis system comprising:
a housing comprising an upper housing and a cartridge removably mounted to the upper housing, a channel disposed through the housing, the channel comprising an inlet end extending through the cartridge, an outlet end extending through the cartridge, and a midportion of the channel extending along an upper surface of the cartridge from the inlet end to the outlet end;
a capillary disposed in the channel in the housing and extending from the inlet end to the outlet end;
a first electrode extending through and depending from at least the cartridge of the housing in association with the capillary at the inlet end and a second electrode extending through and depending from at least the cartridge of the housing in association with the capillary at the outlet end; and
a detector disposed in alignment with a portion of the capillary.

44. The detector module of claim 43, wherein the detector comprises an ultraviolet absorbance detector.

45. The detector module of claim 44, wherein the ultraviolet detector further comprises an optical fiber in communication with an ultraviolet light source and having a termination disposed adjacent to the capillary in the housing, and a photodiode disposed on an opposite side of the capillary in alignment with the termination of the optical fiber.

46. The detector module of claim 45, further comprising an amplifier element in communication with the photodiode.

47. The detector module of claim 46, wherein the amplifier element and photodiode are disposed in a shielded cavity.

48. The detector module of claim 47, wherein a conductive coating is disposed on wall surfaces of the cavity.

49. The detector module of claim 45, wherein the photodiode and the amplifier element are disposed in the cartridge.

50. The detector module of claim 49, further comprising a connector disposed on the cartridge of the housing for connection to a cooperative portion of the housing.

51. The detector module of claim 43, wherein the detector comprises a laser induced fluorescence detector.

52. The detector module of claim 51, further comprising an input optical fiber disposed to transmit light from a laser source having a termination adjacent a capillary disposed in the channel to direct light through the capillary at an acute angle to an axis of the capillary, wherein the excitation light from the capillary is orthogonal to the detector.

53. The detector module of claim 52, wherein the acute angle is greater than a critical angle at which light is reflected away from the capillary.

54. The detector module of claim 52, further comprising an area disposed in the housing on an opposite side of the capillary from the termination of the optical fiber and in axial alignment with the optical fiber.

55. The detector module of claim 51, further comprising an input excitation light path disposed through the housing, the input excitation light path having an excitation light axis crossing the capillary, and a collection optical assembly having a collection optical axis, the excitation axis and the collection optical axis disposed orthogonally.

56. The detector module of claim 55, the collection optical assembly comprising an objective lens assembly configured to maximize an amount of light collection from the capillary.

57. The detector module of claim 56, wherein the objective lens assembly is configured to direct light from the capillary onto substantially parallel paths.

58. The detector module of claim 55, wherein the optical collection assembly includes an interference filter configured to block excitation energy and to pass fluorescent energy.

59. The detector module of claim 55, wherein optical collection assembly comprises a focusing lens disposed to create an image from the capillary.

60. The detector module of claim 55, wherein the optical collection assembly comprises a mask configured to prevent passage of extraneous sources of light.

61. The detector module of claim 55, further comprising a photomultiplier tube sensor aligned on the collection optical axis of the collection assembly.

62. The detector module of claim 43, wherein the detector module further comprises a temperature regulating mechanism operative to maintain the capillary at a selected temperature.

63. The detector module of claim 62, wherein the temperature regulating mechanism further comprises a heat sink.

64. The detector module of claim 43, wherein the detector module further comprises a mechanism configured to be lifted by an arm assembly of a capillary electrophoresis system.

65. The detector module of claim 43, wherein the midportion of the channel extends along a straight line from the inlet end to the outlet end.

66. A detector module for cooperation with a capillary electrophoresis system comprising:

a housing having a channel therethrough;

a capillary disposed in the channel in the housing and extending from an inlet end to an outlet end;

a first electrode depending from the housing in association with the capillary at the inlet end and a second electrode depending from the housing in association with the capillary at the outlet end;

a detector disposed in alignment with a portion of the capillary; and a temperature regulating mechanism operative to maintain the capillary at a selected temperature comprising a cooling channel formed in the housing for a coolant to circulate in the coolant channel.

67. A detector module for cooperation with a capillary electrophoresis system comprising:

a housing having a channel therethrough;

a capillary disposed in the channel in the housing and extending from an inlet end to an outlet end;

a first electrode depending from the housing in association with the capillary at the inlet end and a second electrode depending from the housing in association with the capillary at the outlet end;

a detector disposed in alignment with a portion of the capillary; and a sealing element at the inlet end and the outlet end operative to seal a respective capillary and associated electrode to a working well.

68. The detector module of claim 67, wherein the sealing element is an O-ring.

69. A detector module for cooperation with a capillary electrophoresis system comprising:

a housing having a channel therethrough;

a capillary disposed in the channel in the housing and extending from an inlet end to an outlet end;

a first electrode depending from the housing in association with the capillary at the inlet end and a second electrode depending from the housing in association with the capillary at the outlet end;

a detector disposed in alignment with a portion of the capillary; and a liftable mechanism comprising a magnetizable plate configured to be lifted by an arm assembly of the capillary electrophoresis system.

70. A capillary electrophoresis system comprising:

a base;

a plurality of wells disposed on the base;

an arm assembly mounted to the base and movable in three dimensions;

a detector docking station mounted to the base, a pair of electrodes are disposed on the docking station; and a detector module comprising a capillary extending from an inlet end to an outlet end, and a detector aligned with a portion of the capillary, the arm assembly operative to move the detector module from the detector docking station to a working position with the capillary inlet end disposed in a selected well and the capillary outlet end disposed in a corresponding selected well.

* * * * *

UNITED STATES PATENT AND TRADEMARK OFFICE
CERTIFICATE OF CORRECTION

PATENT NO. : 6,783,649 B2  
DATED : August 31, 2004  
INVENTOR(S) : Herbert J. Hedberg et al.

It is certified that error appears in the above-identified patent and that said Letters Patent is hereby corrected as shown below:

Column 4,  
Line 26, "LIP" should read -- LIF --;

Column 5,  
Line 11, "rnicrotiter" should read -- microtiter --;

Column 10,  
Line 47, "ann" should read -- arm --;  
Line 64, "via)," should read -- vial, --;

Column 11,  
Line 58, "inJ.et" should read -- inlet --;

Column 15,  
Line 41, "irnbedded" should read -- imbedded --;

Column 16,  
Line 59, "paralleL" should read -- parallel --; and

Column 19,  
Line 26, "microtite" should read -- microtiter --.

Signed and Sealed this

Twenty-first Day of March, 2006

JON W. DUDAS  
*Director of the United States Patent and Trademark Office*